US012403131B2

(12) United States Patent
Decrette et al.

(10) Patent No.: US 12,403,131 B2
(45) Date of Patent: Sep. 2, 2025

(54) AFABICIN FORMULATION, METHOD FOR MAKING THE SAME AND USES THEREOF

(71) Applicant: Debiopharm International S.A., Lausanne (CH)

(72) Inventors: Marie Decrette, Publier (FR); Aude Anne-Laure Colin, Publier (FR); Sebastien Chabaud, Riehen (CH)

(73) Assignee: Debiopharm International S.A., Lausanne (CH)

( * ) Notice: Subject to any disclaimer, the term of this patent is extended or adjusted under 35 U.S.C. 154(b) by 827 days.

(21) Appl. No.: 17/430,616

(22) PCT Filed: Feb. 14, 2020

(86) PCT No.: PCT/EP2020/053882
§ 371 (c)(1),
(2) Date: Aug. 12, 2021

(87) PCT Pub. No.: WO2020/165407
PCT Pub. Date: Aug. 20, 2020

(65) Prior Publication Data
US 2022/0142993 A1    May 12, 2022

(30) Foreign Application Priority Data
Feb. 14, 2019   (EP) ..................... 19157255

(51) Int. Cl.
*A61K 31/437*   (2006.01)
*A61K 9/20*   (2006.01)
*A61K 31/40*   (2006.01)

(52) U.S. Cl.
CPC .............. *A61K 31/437* (2013.01); *A61K 9/20* (2013.01); *A61K 31/40* (2013.01)

(58) Field of Classification Search
CPC ......... A61K 31/40; A61K 9/20; A61K 31/437
See application file for complete search history.

(56) References Cited

U.S. PATENT DOCUMENTS

| | | |
|---|---|---|
| 3,828,068 A | 8/1974 | Minieri |
| 4,154,943 A | 5/1979 | Kuehne |
| 4,977,159 A | 12/1990 | Sevrin et al. |
| 5,416,193 A | 5/1995 | Desai |
| 5,614,551 A | 3/1997 | Dick et al. |
| 5,624,941 A | 4/1997 | Barth et al. |
| 5,932,743 A | 8/1999 | Collini et al. |
| 5,985,867 A | 11/1999 | Rodgers et al. |
| 5,989,832 A | 11/1999 | Trias et al. |
| 6,133,260 A | 10/2000 | Matzke et al. |
| 6,174,878 B1 | 1/2001 | Gamache et al. |
| 6,184,380 B1 | 2/2001 | Chiu et al. |
| 6,187,341 B1 | 2/2001 | Johnson et al. |
| 6,194,429 B1 | 2/2001 | Guinn et al. |
| 6,194,441 B1 | 2/2001 | Roberts et al. |
| 6,198,000 B1 | 3/2001 | Hawkins |
| 6,221,859 B1 | 4/2001 | Dorso et al. |
| 6,221,864 B1 | 4/2001 | Hirayama et al. |
| 6,235,908 B1 | 5/2001 | Fey |
| 6,239,113 B1 | 5/2001 | Dawson et al. |
| 6,239,141 B1 | 5/2001 | Allen et al. |
| 6,248,363 B1 | 6/2001 | Patel et al. |
| 6,267,985 B1 | 7/2001 | Chen et al. |
| 6,277,836 B1 | 8/2001 | Borody |
| 6,288,239 B1 | 9/2001 | Hollingsworth et al. |
| 6,291,462 B1 | 9/2001 | Bartholomaeus et al. |
| 6,294,192 B1 | 9/2001 | Patel et al. |
| 6,303,572 B1 | 10/2001 | Rowe |
| 6,309,663 B1 | 10/2001 | Patel et al. |
| 6,333,045 B1 | 12/2001 | Yasueda et al. |
| 6,340,689 B1 | 1/2002 | Dubois et al. |
| 6,346,391 B1 | 2/2002 | Oethinger et al. |
| 6,367,985 B1 | 4/2002 | Lee et al. |
| 6,372,752 B1 | 4/2002 | Staveski et al. |
| 6,388,070 B1 | 5/2002 | Deshpande et al. |
| 6,395,746 B1 | 5/2002 | Caale et al. |
| 6,399,629 B1 | 6/2002 | Chamberland et al. |
| 6,406,880 B1 | 6/2002 | Thornton |
| 6,423,341 B1 | 7/2002 | Yamaguchi |

(Continued)

FOREIGN PATENT DOCUMENTS

| | | |
|---|---|---|
| CA | 2444597 A1 | 10/2002 |
| CA | 2568914 A1 | 12/2005 |

(Continued)

OTHER PUBLICATIONS

Flamm, R. K.; et al. "Activity of Debio1452, a FabI Inhibitor with Potent Activity against *Staphylococcus aureus* and Coagulase-Negative *Staphylococcus* spp., Including Multidrug-Resistant Strains" 2015, Antimicrobial Agents and Chemotherapy, vol. 59, pp. 2583-2587. (Year: 2015).*

Defres, S.; et al. "MRSA as a cause of lung infection including airway infection, community acquired pneumonia and hospital-acquired pneumonia" 2009, Eur. Respir. J., vol. 34, pp. 1470-1476. (Year: 2009).*

Yang, X.-F.; et al. "The influence of amino acids on aztreonam spray-dried powders for inhalation" 2015, Asian J. Pharm. Sci. 2015, vol. 10, pp. 541-548. (Year: 2015).*

Huang, Y.; et al. "Amino acids as co-amorphous excipients for tackling the poor aqueous solubility of valsartan" 2017, Pharmaceutical Development and Technology, vol. 22, pp. 69-76. (Year: 2017).*

U.S. Appl. No. 14/010,166, filed Aug. 26, 2013, Partridge et al.

(Continued)

*Primary Examiner* — Eric Olson
*Assistant Examiner* — Benjamin M Brandsen
(74) *Attorney, Agent, or Firm* — Wolf, Greenfield & Sacks, P.C.

(57) ABSTRACT

The present invention provides Afabicin-containing solid pharmaceutical compostions exhibiting superior dissolution characteristics. This beneficial effect is accomplished by the presence of a histidine compound for manufacturing the compositions. The present invention further provides methods for making such compositions and uses thereof.

18 Claims, 4 Drawing Sheets

(56) References Cited

U.S. PATENT DOCUMENTS

| | | |
|---|---|---|
| 6,423,741 B1 | 7/2002 | Khanuja et al. |
| 6,428,579 B1 | 8/2002 | Valentini |
| 6,432,444 B1 | 8/2002 | Fischetti et al. |
| 6,432,670 B1 | 8/2002 | Payne et al. |
| 6,436,980 B1 | 8/2002 | Leaer et al. |
| 6,441,162 B2 | 8/2002 | Yasui et al. |
| 6,448,054 B1 | 9/2002 | Poznansky et al. |
| 6,448,238 B1 | 9/2002 | Shoichet et al. |
| 6,448,449 B2 | 9/2002 | Larrow |
| 6,451,339 B2 | 9/2002 | Patel et al. |
| 6,451,816 B1 | 9/2002 | Biedermann et al. |
| 6,461,607 B1 | 10/2002 | Farmer |
| 6,461,829 B1 | 10/2002 | Kahne |
| 6,465,429 B1 | 10/2002 | Hancock et al. |
| 6,468,964 B1 | 10/2002 | Rowe |
| 6,469,046 B1 | 10/2002 | Daines et al. |
| 6,486,148 B2 | 11/2002 | Savage et al. |
| 6,486,149 B2 | 11/2002 | Onodera et al. |
| 6,486,165 B2 | 11/2002 | Zhang et al. |
| 6,489,318 B1 | 12/2002 | Copar et al. |
| 6,492,351 B1 | 12/2002 | Zhang et al. |
| 6,495,158 B1 | 12/2002 | Buseman et al. |
| 6,495,161 B1 | 12/2002 | Soon-Shiong et al. |
| 6,495,551 B1 | 12/2002 | Betts et al. |
| 6,497,886 B1 | 12/2002 | Breitenbach et al. |
| 6,500,459 B1 | 12/2002 | Chhabra et al. |
| 6,500,463 B1 | 12/2002 | van Lengerich |
| 6,503,539 B2 | 1/2003 | Gestrelius et al. |
| 6,503,881 B2 | 1/2003 | Krieger et al. |
| 6,503,903 B1 | 1/2003 | Miller et al. |
| 6,503,906 B1 | 1/2003 | Lee |
| 6,503,908 B1 | 1/2003 | Maw |
| 6,503,953 B2 | 1/2003 | Vyden |
| 6,503,955 B1 | 1/2003 | Dobrozsi et al. |
| 6,509,327 B1 | 1/2003 | Cagle et al. |
| 6,514,535 B2 | 2/2003 | Marchant |
| 6,514,541 B2 | 2/2003 | Khanuja et al. |
| 6,514,953 B1 | 2/2003 | Armitage et al. |
| 6,514,962 B1 | 2/2003 | Shibatani et al. |
| 6,514,986 B2 | 2/2003 | de Souza et al. |
| 6,515,113 B2 | 2/2003 | Raymond et al. |
| 6,517,827 B1 | 2/2003 | Bacon Kurtz et al. |
| 6,518,239 B1 | 2/2003 | Kuo et al. |
| 6,518,263 B1 | 2/2003 | Nishitani et al. |
| 6,518,270 B1 | 2/2003 | Amin et al. |
| 6,518,487 B1 | 2/2003 | Lowe et al. |
| 6,521,408 B1 | 2/2003 | Kawasaki |
| 6,525,066 B2 | 2/2003 | Fukumoto et al. |
| 6,527,759 B1 | 3/2003 | Tachibana et al. |
| 6,528,089 B1 | 3/2003 | Kothrade et al. |
| 6,531,126 B2 | 3/2003 | Farmer |
| 6,531,291 B1 | 3/2003 | Kabbash et al. |
| 6,531,465 B1 | 3/2003 | Ascher et al. |
| 6,531,508 B1 | 3/2003 | Nomura et al. |
| 6,531,649 B1 | 3/2003 | Mannerloef et al. |
| 6,559,172 B1 | 5/2003 | Heerding et al. |
| 6,573,272 B1 | 6/2003 | Miller et al. |
| 6,673,941 B2 | 1/2004 | Heerding et al. |
| 6,703,684 B2 | 3/2004 | Udrea et al. |
| 6,730,684 B1 | 5/2004 | Miller et al. |
| 6,762,201 B1 | 7/2004 | Miller et al. |
| 6,765,005 B2 | 7/2004 | Miller et al. |
| 6,821,746 B2 | 11/2004 | DeWolf, Jr. et al. |
| 6,846,819 B1 | 1/2005 | Miller et al. |
| 6,951,729 B1 | 10/2005 | Dewolf, Jr. et al. |
| 6,964,970 B2 | 11/2005 | Miller et al. |
| 6,995,254 B1 | 2/2006 | Payne et al. |
| 7,048,926 B2 | 5/2006 | Brandt et al. |
| 7,049,310 B2 | 5/2006 | Burgess et al. |
| 7,250,424 B2 | 7/2007 | Burgess et al. |
| 7,449,458 B2 | 11/2008 | Bhamidipati et al. |
| 7,524,843 B2 | 4/2009 | Miller et al. |
| 7,538,108 B2 | 5/2009 | Singh et al. |
| 7,557,125 B2 | 7/2009 | Miller et al. |
| 7,563,892 B1 | 7/2009 | Singh et al. |
| 7,741,339 B2 | 6/2010 | Burgess et al. |
| 7,790,709 B2 | 9/2010 | Berman et al. |
| 7,790,716 B2 | 9/2010 | Miller et al. |
| 7,879,872 B2 | 2/2011 | Berman et al. |
| 7,989,448 B2 | 8/2011 | Singh et al. |
| 8,003,673 B2 | 8/2011 | Alder et al. |
| 8,153,652 B2 | 4/2012 | Burgess et al. |
| 8,163,902 B2 | 4/2012 | Bhamidipati et al. |
| 8,173,646 B2 | 5/2012 | Miller et al. |
| 8,211,888 B2 | 7/2012 | Singh et al. |
| 8,211,889 B2 | 7/2012 | Singh et al. |
| 8,263,613 B2 | 9/2012 | Pauls et al. |
| 8,318,720 B2 | 11/2012 | Pauls et al. |
| 8,450,307 B2 | 5/2013 | Sargent et al. |
| 8,741,855 B2 | 6/2014 | Quave et al. |
| 8,901,105 B2 | 12/2014 | Partridge et al. |
| 10,035,813 B2 | 7/2018 | Partridge et al. |
| 10,751,351 B2 | 8/2020 | Vuagniaux et al. |
| 2001/0016662 A1 | 8/2001 | Golik et al. |
| 2003/0232850 A1 | 12/2003 | Miller et al. |
| 2004/0053814 A1 | 3/2004 | Brandt et al. |
| 2004/0127403 A1 | 7/2004 | Parenti et al. |
| 2004/0147580 A1 | 7/2004 | Burgess et al. |
| 2005/0250810 A1 | 11/2005 | Miller et al. |
| 2006/0142265 A1 | 6/2006 | Berman et al. |
| 2006/0183908 A1 | 8/2006 | Berman et al. |
| 2006/0211657 A1 | 9/2006 | Singh et al. |
| 2006/0234983 A1 | 10/2006 | Singh et al. |
| 2008/0125423 A1 | 5/2008 | Miller et al. |
| 2009/0042927 A1 | 2/2009 | Pauls et al. |
| 2009/0156578 A1 | 6/2009 | Pauls et al. |
| 2009/0221699 A1 | 9/2009 | Burgess et al. |
| 2010/0130470 A1 | 5/2010 | Pauls et al. |
| 2011/0124633 A1 | 5/2011 | Berman et al. |
| 2012/0010127 A1 | 1/2012 | Berman et al. |
| 2013/0237523 A1 | 9/2013 | Pauls et al. |
| 2013/0281442 A1 | 10/2013 | Hafkin |
| 2014/0051666 A1 | 2/2014 | Partridge et al. |
| 2014/0107106 A1 | 4/2014 | Sargent et al. |
| 2015/0065415 A1 | 3/2015 | Partridge et al. |
| 2019/0054100 A1 | 2/2019 | Vuagniaux et al. |
| 2023/0126947 A1 | 4/2023 | Nowakowska et al. |

FOREIGN PATENT DOCUMENTS

| | | |
|---|---|---|
| CA | 2776849 A1 | 5/2011 |
| CN | 101415701 A | 4/2009 |
| CN | 102675311 A | 9/2012 |
| CN | 104684922 A | 6/2015 |
| CN | 108778286 A | 11/2018 |
| EP | 0407200 A1 | 1/1991 |
| EP | 0953570 A1 | 11/1999 |
| EP | 1000935 A1 | 5/2000 |
| EP | 3923914 A1 | 12/2021 |
| HU | 0203122 B | 5/1991 |
| HU | 210679 B | 6/1995 |
| JP | 11-302173 A | 11/1999 |
| JP | 2005-519984 A | 7/2005 |
| JP | 2015-521617 A | 7/2015 |
| JP | 2019-512467 A | 5/2019 |
| WO | WO 93/04035 A1 | 3/1993 |
| WO | WO 95/18619 A1 | 7/1995 |
| WO | WO 96/00730 A1 | 1/1996 |
| WO | WO 97/48696 A1 | 12/1997 |
| WO | WO 98/57952 A1 | 12/1998 |
| WO | WO 99/24406 A1 | 5/1999 |
| WO | WO 00/27628 A1 | 5/2000 |
| WO | WO 00/57933 A1 | 10/2000 |
| WO | WO 01/26652 A1 | 4/2001 |
| WO | WO 01/26654 A1 | 4/2001 |
| WO | WO 01/27103 A1 | 4/2001 |
| WO | WO 01/41573 A1 | 6/2001 |
| WO | WO 01/48248 A2 | 7/2001 |
| WO | WO 01/70172 A2 | 9/2001 |
| WO | WO 02/10332 A1 | 2/2002 |
| WO | WO 02/42273 A2 | 5/2002 |
| WO | WO 02/48097 A1 | 6/2002 |
| WO | WO 02/064572 A1 | 8/2002 |
| WO | WO 03/086396 A1 | 10/2003 |

(56) References Cited

FOREIGN PATENT DOCUMENTS

| WO | WO 03/088897 A2 | 10/2003 |
|---|---|---|
| WO | WO 2004/014869 A2 | 2/2004 |
| WO | WO 2004/052890 A1 | 6/2004 |
| WO | WO 2004/082586 A1 | 9/2004 |
| WO | WO 2005/090367 A1 | 9/2005 |
| WO | WO 2006/130629 A2 | 12/2006 |
| WO | WO 2007/053131 A2 | 5/2007 |
| WO | WO 2007/067416 A2 | 6/2007 |
| WO | WO 2008/009122 A1 | 1/2008 |
| WO | WO 2008/064274 A1 | 5/2008 |
| WO | WO 2008/098374 A1 | 8/2008 |
| WO | WO 2009/003136 A1 | 12/2008 |
| WO | WO 2010/151689 A1 | 12/2010 |
| WO | WO 2010/151711 A1 | 12/2010 |
| WO | WO 2011/002999 A1 | 1/2011 |
| WO | WO 2011/061214 A1 | 5/2011 |
| WO | WO 2011/156811 A2 | 12/2011 |
| WO | WO 2013/080222 A1 | 6/2013 |
| WO | WO 2013/190384 A1 | 12/2013 |
| WO | WO 2015/118496 A1 | 8/2015 |
| WO | WO 2017/144717 A1 | 8/2017 |
| WO | WO 2020/249731 A1 | 12/2020 |

OTHER PUBLICATIONS

U.S. Appl. No. 14/534,573, filed Nov. 6, 2014, Partridge et al.
U.S. Appl. No. 16/079,804, filed Aug. 24, 2018, Vuagniaux et al.
U.S. Appl. No. 17/618,882, filed Dec. 13, 2021, Nowakowska et al.
HU P0203122, Dec. 31, 2003, Hungarian Search Report.
PCT/US2006/045903, Sep. 12, 2007, International Search Report.
PCT/CA2008/000300, Jun. 5, 2008, International Search Report.
PCT/CA2007/001277, Jan. 20, 2009, International Preliminary Report on Patentability.
PCT/US2011/040187, Nov. 30, 2011, International Search Report and Written Opinion.
EP 11793310.1, Oct. 30, 2013, European Search Report.
PCT/IB2013/001780, Dec. 3, 2013, International Search Report and Written Opinion.
EP 8714623.9, Jul. 16, 2014, European Search Report.
PCT/EP2017/054470, May 26, 2017, International Search Report and Written Opinion.
PCT/EP2020/053882, Apr. 1, 2020, International Search Report and Written Opinion.
PCT/EP2020/053882, Aug. 26, 2021, International Preliminary Report on Patentability.
PCT/EP2020/066305, Oct. 6, 2020, International Search Report and Written Opinion.
PCT/EP2020/066305, Dec. 14, 2021, International Preliminary Report on Patentability.
Hungarian Search Report mailed Dec. 31, 2003 for Hungarian Application No. P0203122.
International Search Report dated Sep. 12, 2007 for PCT/US2006/045903.
International Search Report dated Jun. 5, 2008 for PCT/CA2008/000300.
International Preliminary Report on Patentability mailed Jan. 20, 2009 for International Application No. PCT/CA2007/001277.
International Search Report and Written Opinion mailed Nov. 30, 2011 for International Application No. PCT/US2011/040187.
European Search Report mailed Oct. 30, 2013 for European Application No. 11793310.1.
International Search Report and Written Opinion mailed Dec. 3, 2013 for International Application No. PCT/IB2013/001780.
European Search Report dated Jul. 16, 2014 for European Application No. 08714623.9.
International Search Report and Written Opinion mailed May 26, 2017 for International Application No. PCT/EP2017/054470.
International Search Report and Written Opinion mailed Apr. 1, 2020 for International Application No. PCT/EP2020/053882.

International Preliminary Report on Patentability mailed Aug. 26, 2021 for International Application No. PCT/EP2020/053882.
International Search Report and Written Opinion mailed Oct. 6, 2020 for International Application No. PCT/EP2020/066305.
International Preliminary Report on Patentability mailed Dec. 14, 2021 for International Application No. PCT/EP2020/066305.
Abou-Gharbia et al., Psychotropic agents: synthesis and antipsychotic activity of substituted beta-carbolines. J Med Chem. Jun. 1987;30(6):1100-5. doi: 10.1021/jm00389a022.
Ahsan et al. Reserpine analogues: synthesis of β-carboline derivative. J. Chem. Soc. 1963:3928-30. doi: 10.1039/JR9630003928.
Annesley et al., Glucuronidation of prodrug reactive site: isolation and characterization of oxymethylglucuronide metabolite of fosphenytoin. Clin Chem. May 2001;47(5):910-8.
Arakawa et al., Biotechnology applications of amino acids in protein purification and formulations. Amino Acids. Nov. 2007;33(4):587-605. doi: 10.1007/s00726-007-0506-3. Epub Mar. 16, 2007.
Arora et al., Cutaneous microcirculation in the neuropathic diabetic foot improves significantly but not completely after successful lower extremity revascularization. J Vasc Surg. Mar. 2002;35(3):501-5.
Banu et al., Spectrum of bacteria associated with diabetic foot ulcer and biofilm formation: A prospective study. Australas Med J. Sep. 30, 2015;8(9):280-5. doi: 10.4066/AMJ.2015.2422.eCollection 2015.
Barkema et al., Invited Review: The role of cow, pathogen, and treatment regimen in the therapeutic success of bovine *Staphylococcus aureus* mastitis. J Dairy Sci. Jun. 2006;89(6):1877-95. doi: 10.3168/jds.S0022-0302(06)72256-1.
Bastin et al., Salt Selection and Optimisation Procedure for Pharmaceutical New Chemical Entities, Organic Process Res. & Dev., 2000;4(5):427-35.
Berge et al., Pharmaceuticals Salts, J. of Pharm. Sciences, 1977;66(1):1-19.
Bergler et al., Protein EnvM is the NADH-dependent enoyl-ACP reductase (FabI) of *Escherichia coli*. J Biol Chem. Feb. 25, 1994;269(8):5493-6.
Boffeli et al., In-office distal Symes lesser toe amputation: a safe, reliable, and cost-effective treatment of diabetes-related tip of toe ulcers complicated by osteomyelitis. J Foot Ankle Surg. Nov.-Dec. 2014;53(6):720-6. doi: 10.1053/j.jfas.2014.04.020. Epub Jul. 22, 2014.
Chen et al., Synthesis and antibacterial evaluation of certain quinolone derivatives. J Med Chem. Jul. 5, 2001;44(14):2374-7. doi: 10.1021/jm0100335.
Claus et al., Formaldehydabspaltende Phenolcarbonsaurederivte Monatsh. Chem. 1966;97:271-9.
Database CA on STN, AN 7:66733, Rosenmund et al., "Chemistry of indole II. Beckmann and Schmidt Rearranements of Some Indole Ketones," Chem. Ber., 103 2: 496-509 1970.
Database CAOLD on STN, AN CA51:10524d, Hellman et al., "N-Mannich bases (VI) condensation of N-dialkylaminomethylbenzamides with amines and amides, (VII) N-acylaminomethylation of indole," Direct Submission, 1953.
Database CAPLUS on STN AN 1999:325910 Aslanian, et al., "Preparation of (phenvlaikv)imidazoles as H3 receptor antagonists," W099/24406. 1999.
Database CAPLUS on STN, AN 1977:439214. Misztal et al., "Synthesis and pharmacologic properties of pyridoyl derivatives of 3-methylaminoindole 2-methyltryptamine and isotryptamine," Arch Immuno Ther Exp., 24(6):851-862, 1976.
Database CAPLUS on STN, AN 1986:68547, Stuetz et al., "Synthesis and Structure-activity relationships of naftifine-related allvlamine antimvcotics," J. Med. Chem., 29(1):112-25, 1986.
Database CAPLUS on STN, AN 1991:428908, Fuse et al., "Preparation of cinnamamide derivatives an antihyperlipidemics," EP407200A1, 1991.
Database Crossfile Beilstein, 1966, Database accession No. 2819049, 2819050, XP002216033.
Dykhuizen, Santa Rosalia revisited: why are there so many species of bacteria? Antonie Van Leeuwenhoek. Jan. 1998;73(1):25-33. doi: 10.1023/a:1000665216662.

(56) References Cited

OTHER PUBLICATIONS

Ettmayer et al., Lessons learned from marketed and investigational prodrugs. J Med Chem. May 6, 2004;47(10):2393-404. doi: 10.1021/jm0303812.
Foroumadi et al., Synthesis and in vitro antibacterial evaluation of N-[5-(5-nitro-2-thienyl)-1,3,4-thiadiazole-2-yl] piperazinyl quinolones. Eur J Med Chem. Sep. 2003;38(9):851-4. doi: 10.1016/s0223-5234(03)00148-x.
Gokarn et al., Amino Acids. In: Excipient Development for Pharmaceutical, Biotechnology, and Drug Delivery Systems. 2006. Katdare et al., Eds. pp. 299-300.
Grassberger et al., Preparation and antibacterial activities of new 1,2,3-diazaborine derivatives and analogues. J Med Chem. Aug. 1984;27(8):947-53. doi: 10.1021/jm00374a003.
Heath et al., A triclosan-resistant bacterial enzyme. Nature. Jul. 13, 2000;406(6792):145-6. doi: 10.1038/35018162. Erratum in: Nature Aug. 24, 2000;406(6798):848.
Heath et al., Regulation of fatty acid elongation and initiation by acyl-acyl carrier protein in *Escherichia coli*. J Biol Chem. Jan. 26, 1996;271(4):1833-6. doi: 10.1074/jbc.271.4.1833.
Heck, Palladium-Catalyzed Vinylation of Organic Halides. Organic Reactions. 1982;27:345-90. doi: http://dx.doi.org/10.1002/0471264180.or027.02.
Heimbach et al., Absorption rate limit considerations for oral phosphate prodrugs. Pharm Res. Jun. 2003;20(6):848-56. doi: 10.1023/a:1023827017224.
Hill et al., The Effects of Peripheral Vascular Disease with Osteomyelitis in the Diabetic Foot. Am. J. Surg. Apr. 1999;177:282-6.
Himmler et al., Synthesis and antibacterial in vitro activity of novel analogues of nematophin. Bioorg Med Chem Lett. Aug. 4, 1998;8(15):2045-50. doi: 10.1016/s0960-894x(98)00358-8.
Jossang-Yanagida et al., Tetrahydropyridoazepines and Tetrahydropyridoazepinones from the Corresponding Dihydroquinolones. J. Heterocyclic Chemistry. Mar. 1978;15(2):249-51. doi: 10.1002/jhet.5570150213.
Kaplan et al., Abstract F1-2005 "In Vitro and In Vivo Absorption Properties of AFN-1252, a Novel Specific-Spectrum Anti-Staphylcoccal Agent," American Society for Microbiology 49th ICAAC Meeting Abstract, Tuesday, Sep. 15, 2009.
Kaplan et al., Abstract F1-2006 "Correlation of AFN-1252 Phase 0 Microdosing and Phase 1 Pharmacokinetics" American Society for Microbiology 49th ICAAC Meeting Abstract, Tuesday, Sep. 15, 2009.
Kaplan et al., In vitro activity (MICs and rate of kill) of AFN-1252, a novel FabI inhibitor, in the presence of serum and in combination with other antibiotics. J Chemother. Feb. 2013;25(1):18-25. doi: 10.1179/1973947812Y.0000000063.
Karchmer et al., Is there a future for FabI inhibitors as antibacterial agents? Clin. Invest. 2013;3(8):707-9.
Karlowsky et al., AFN-1252, a FabI inhibitor, demonstrates a *Staphylococcus*-specific spectrum of activity. Antimicrob Agents Chemother. Aug. 2009;53(8):3544-8. doi: 10.1128/AAC.00400-09. Epub Jun. 1, 2009.
Karlowsky et al., In vitro activity of API-1252, a novel FabI inhibitor, against clinical isolates of *Staphylococcus aureus* and *Staphylococcus epidermidis*. Antimicrob Agents Chemother. Apr. 2007;51(4):1580-1. doi: 10.1128/AAC.01254-06. Epub Jan. 12, 2007.
Kearney et al., The in vitro enzymic labilities of chemically distinct phosphomonoester prodrugs. Pharm Res. Apr. 1992;9(4):497-503. doi: 10.1023/a:1015840329786.
Lakemeyer et al., Thinking Outside the Box-Novel Antibacterials To Tackle the Resistance Crisis. Angew Chem Int Ed Engl. Oct. 26, 2018;57(44):14440-14475. doi: 10.1002/anie.201804971. Epub Oct. 11, 2018.
Leppik et al., Pharmacokinetics and safety of a phenytoin prodrug given i.v. or i.m. in patients. Neurology. Mar. 1990;40(3 Pt 1):456-60. doi: 10.1212/wnl.40.3_part_1.456.
Levy et al., Molecular basis of triclosan activity. Nature. Apr. 1, 1999;398(6726):383-4. doi: 10.1038/18803.

Li et al., Synthesis and Antistatphyloccocal Activity of Nematophin and its Analogs, Bioorganic & Medicinal Chemistry Letters Oxford, GB, May 2, 19970;7(10):1349-1352.
Lipsky et al., Treating diabetic foot osteomyelitis primarily with surgery or antibiotics: have we answered the question? Diabetes Care. 2014;37(3):593-5. doi: 10.2337/dc13-2510.
Lovati et al., Does PGE1 vasodilator prevent orthopaedic implant-related infection in diabetes?
McMurry et al., Triclosan targets lipid synthesis. Nature. Aug. 6, 1998;394(6693):531-2. doi: 10.1038/28970.
Menetrey et al., Bone and Joint Tissue Penetration of the *Staphylococcus*-Selective Antibiotic Afabicin in Patients Undergoing Elective Hip Replacement Surgery. Antimicrob Agents Chemother. Feb. 2, 20196;63(3):e01669-18. doi: 10.1128/AAC.01669-18.
Menetrey et al., Mass Balance, Pharmacokinetics and Metabolism of the Antimicrobial Afabicin Following Intravenous and Oral Administration in Humans. Clin Ther. Aug. 1, 2017;39(8):E65. doi: 10.1016/j.clinthera.2017.05.200.
Miller et al., Discovery of aminopyridine-based inhibitors of bacterial enoyl-ACP reductase (FabI). J Med Chem. Jul. 18, 2002;45(15):3246-56. doi: 10.1021/jm020050+.
Misztal et al., Synthesis and pharmacologic properties of pyridoyl derivatives of 3-methylaminoindole 2-methyltryptamine and isotryptamine. Arch Immunol Ther Exp (Warsz). 1976;24(6):851-62.
Nicolau et al., Therapeutic options for diabetic foot infections: a review with an emphasis on tissue penetration characteristics. J Am Podiatr Med Assoc. Jan.-Feb. 2010;100(1):52-63. Review.
Pachter et al., The Chemistry of Hortiamine and 6-Methoxyhetsinine. J. Amer. Chem. Feb. 1961;83(3):635-42. doi: 10.1021/ja01464a032.
Payne et al., Bacterial fatty-acid biosynthesis: a genomics-driven target for antibacterial drug discovery. Drug Discov Today. May 1, 2001;6(10):537-544. doi: 10.1016/s1359-6446(01)01774-3.
Payne et al., Discovery of a novel and potent class of FabI-directed antibacterial agents. Antimicrob Agents Chemother. Oct. 2002;46(10):3118-24. doi: 10.1128/AAC.46.10.3118-3124.2002.
Pee et al., A FASII Inhibitor Prevents Staphylococcal Evasion of Daptomycin by Inhibiting Phospholipid Decoy Production. Antimicrob Agents Chemother. Mar. 27, 2019;63(4):e02105-18. doi: 10.1128/AAC.02105-18.
Ramnauth et al., 2,3,4,5-Tetrahydro-1H-pyrido[2,3-b and e][1,4]diazepines as inhibitors of the bacterial enoyl ACP reductase, FabI. Bioorg Med Chem Lett. Sep. 15, 2009;19(18):5359-62. doi: 10.1016/j.bmcl.2009.07.094. Epub Jul. 23, 2009.
Rautio et al., Prodrugs: design and clinical applications. Nat Rev Drug Discov. Mar. 2008;7(3):255-70. doi: 10.1038/nrd2468. Erratum in: Nat Rev Drug Discov. Mar. 2008;7(3):272.
Rautio et al., Prodrugs—Recent approvals and a glimpse of the pipeline. Eur J Pharm Sci. Nov. 15, 2017;109:146-161. doi: 10.1016/j.ejps.2017.08.002. Epub Aug. 4, 2017.
Rehse et al., Dopaminanaloge 1,2,3,4-Tetrahydro-beta-carboline [Dopamine analogous 1,2,3,4-tetrahydro-beta-carbolines (author's transl)]. Arch Pharm (Weinheim). Jan. 1978;311(1):11-8. German. doi: 10.1002/ardp.19783110104.
Saginur et al., Multiple combination bactericidal testing of staphylococcal biofilms from implant-associated infections. Antimicrob Agents Chemother. Jan. 2006;50(1):55-61. doi: 10.1128/AAC.50.1.55-61.2006.
Seefeld et al., Indole naphthyridinones as inhibitors of bacterial enoyl-ACP reductases FabI and FabK. J Med Chem. Apr. 24, 2003;46(9):1627-35. doi: 10.1021/jm0204035.
Shoji et al., Two Novel Alkaloids from Evodia rutaecarpa. J. Nat. Prod. 1989;52(5):1160-2. doi: 10.1021/np50065a043.
Sladowska et al., Synthesis and properties of amides of 1-benzyl-3-methyl- and 1-butyl-3-phenyl-7-methyl-4-oxo-2-thioxo (2,4-dioxo)-1,2,3,4-tetrahydropyrido-[2,3-d]pyrimidine-6-carboxylic acids. Farmaco Sci. Dec. 1986;41(12):954-63.
Stutz et al., Synthesis and structure-activity relationships of naftifine-related allylamine antimycotics. J Med Chem. Jan. 1986;29(1):112-25. doi: 10.1021/jm00151a019.
Turnowsky et al., envM genes of *Salmonella typhimurium* and *Escherichia coli*. J Bacteriol. Dec. 1989;171(12):6555-65. doi: 10.1128/jb.171.12.6555-6565.1989.

(56) References Cited

OTHER PUBLICATIONS

Varia et al., Phenytoin prodrugs III: water-soluble prodrugs for oral and/or parenteral use. J Pharm Sci. Aug. 1984;73(8):1068-73. doi: 10.1002/jps.2600730812.

Varia et al., Phenytoin prodrugs IV: Hydrolysis of various 3-(hydroxymethyl)phenytoin esters. J Pharm Sci. Aug. 1984;73(8):1074-80. doi: 10.1002/jps.2600730813.

Varia et al., Phenytoin prodrugs V: In vivo evaluation of some water-soluble phenytoin prodrugs in dogs. J Pharm Sci. Aug. 1984;73(8):1080-7. doi: 10.1002/jps.2600730814.

Varia et al., Phenytoin prodrugs VI: In vivo evaluation of a phosphate ester prodrug of phenytoin after parenteral administration to rats. J Pharm Sci. Aug. 1984;73(8):1087-90. doi: 10.1002/jps.2600730815.

Ward et al., Kinetic and structural characteristics of the inhibition of enoyl (acyl carrier protein) reductase by triclosan. Biochemistry. Sep. 21, 1999;38(38):12514-25. doi: 10.1021/bi9907779.

Weiss et al., Efficacy of AFN-1252 and Vancomycin in the Mouse Subcutaneous Abscess Model with Methicillin-Resistant *Staphylococcus aureus*. Interscience Conference on Antimicrobial Agents & Chemotherapy (ICAAC). Jan. 2008;48:277. Abstract, 1 page.

Archer et al., *Staphylococcus aureus* biofilms: properties, regulation, and roles in human disease. Virulence. Sep.-Oct. 2011;2(5):445-59. doi: 10.4161/viru.2.5.17724. Epub Sep. 1, 2011.

Maiden et al., Triclosan depletes the membrane potential in *Pseudomonas aeruginosa* biofilms inhibiting aminoglycoside induced adaptive resistance. PLoS Pathog. Oct. 30, 2020;16(10):e1008529. doi: 10.1371/journal.ppat.1008529.

Maiden et al., Triclosan Is an Aminoglycoside Adjuvant for Eradication of *Pseudomonas aeruginosa* Biofilms. Antimicrob Agents Chemother. May 25, 2018;62(6):e00146-18. doi: 10.1128/AAC.00146-18.

Müller et al., Prodrug approaches for enhancing the bioavailability of drugs with low solubility. Chem Biodivers. Nov. 2009;6(11):2071-83. doi: 10.1002/cbdv.200900114.

\* cited by examiner

AFABICIN FORMULATION, METHOD FOR MAKING THE SAME AND USES THEREOF

CROSS REFERENCE TO RELATED APPLICATIONS(S)

This Application is a National Stage filing under 35 U.S.C. 371 of International Patent Application Serial No. PCT/EP2020/053882, filed Feb. 14, 2020. Foreign priority benefits are claimed under 35 U.S.C. § 119(a)-(d) or 35 U.S.C. § 365(b) of European application number 19157255.1, filed Feb. 14, 2019. The entire contents of these applications are incorporated herein by reference in their entirety.

TECHNICAL FIELD

The present invention relates to pharmaceutical compositions containing Afabicin and especially to histidine compound containing Afabicin formulations. The present invention also relates to methods for manufacturing such formulations as well as uses thereof, in particular for treating bacterial infections.

BACKGROUND OF THE INVENTION

Afabicin is described, as its free acid form or under various salt forms, in WO 2013/190384 A as a prodrug of the active agent known from example 99 of WO 03/088897 A. Afabicin has the following structure (depicted as the free acid form):

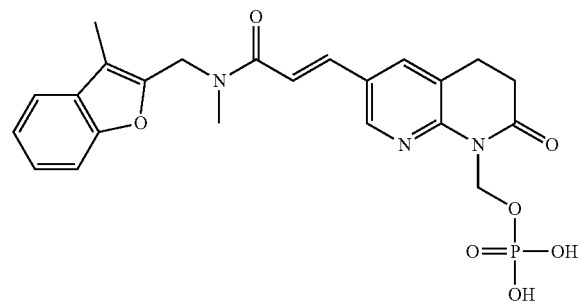 [SMILES: Cc1c(CN(C)C(=O)/C=C/c2cnc3c(c2)CCC(=O)N3COP(=O)(O)O)oc2ccccc12]

In order to be suitable for oral administration, Afabicin must be provided in a formulation that is able to disintegrate at pH of gastric fluid and that is capable of releasing the drug. WO 2013/190384 A describes methods for manufacturing Afabicin as well as formulations containing the same. This document describes various materials as excipients suitable for formulating Afabicin.

However, when trying to develop an Afabicin formulation based on commonly employed excipient materials, incomplete disintegration of the pharmaceutical form and poor dissolution of Afabicin were observed.

OBJECT OF THE INVENTION

It is an object of the present invention to provide pharmaceutical compositions comprising Afabicin, preferably Afabicin Olamine (i.e. the bis-2-ethanolammonium salt of Afabicin, which is sometimes also referred to as the bis-ethanolamine salt of Afabicin), allowing disintegration which exhibit superior dissolution characteristics. It is a further object of the present invention to provide such compositions, which additionally exhibit satisfactory dissolution stability. It is also a further object of the present invention to provide such compositions, which additionally exhibit satisfactory chemical stability. Yet another objective of the present invention is to provide such compositions, which exhibit satisfactory oral bioavailability and therapeutic efficacy. Yet another object of the present invention is to provide such compositions, which are easy to manufacture at low cost.

SUMMARY OF THE INVENTION

The above objectives are accomplished by means of the pharmaceutical compositions comprising Afabicin, as disclosed herein and as specified in the appended claims. In particular, the following pharmaceutical compositions are provided:

1. Solid pharmaceutical composition in the form of a unit dose comprising Afabicin or a pharmaceutically acceptable salt thereof and one or more pharmaceutically acceptable excipients, characterized in that the composition contains a histidine compound.
2. Solid pharmaceutical composition according to item 1, which comprises Afabicin or a pharmaceutically acceptable salt thereof in an amount of from 20 mg to 480 mg.
3. Solid pharmaceutical composition according to item 1 or 2, which contains histidine.
4. Solid pharmaceutical composition according to anyone of items 1 to 3, which is in the form of a tablet, the tablet preferably comprising an internal phase and an external phase, wherein Afabicin or a pharmaceutically acceptable salt thereof is preferably contained only in the internal phase.
5. Solid pharmaceutical composition according to item 4, which contains the histidine compound only in the internal phase.
6. Solid pharmaceutical composition according to anyone of items 1 to 5, which contains a binder selected from the group consisting of povidone, copovidone, poloxamer, polyethylene glycol, magnesium aluminosilicate, gelatin, acacia, dextrin, dextrates, dextrose, polydextrose, guar gum, hydrogenated vegetable oil, liquid glucose, wax, maltose, sucrose, lactose, wax, and mixtures thereof.
7. Solid pharmaceutical composition according to anyone of claims 1 to 6, which contains a diluent selected from the group consisting of mannitol, isomalt, lactose, calcium phosphate, calcium carbonate, calcium sulfate, sucrose, fructose, maltose, xylitol, maltitol, lactitol, trehalose, aluminum silicate, cyclodextrin, dextrose, polydextrose, glucose, dextrin, dextrates, magnesium carbonate and mixtures thereof.
8. Solid pharmaceutical composition according to anyone of items 1 to 7, which contains a surfactant selected from the group consisting of sodium lauryl sulfate, poloxamers, sodium docusate, sodium deoxycholate, sorbitan esters, sucrose esters of fatty acid, tyloxapol, lecithin and polysorbate and mixtures thereof.
9. Solid pharmaceutical composition according to anyone of items 1 to 8, which contains a disintegrant selected from the group consisting of crospovidone, magnesium aluminosilicate, colloidal silicon dioxide, guar gumand mixtures thereof.
10. Solid pharmaceutical composition according to anyone of items 1 to 3 and 6 to 9, which is in the form of a capsule containing Afabicin or a pharmaceutically acceptable salt thereof and one or more pharmaceutically acceptable excipients in the form of a powder or granulate.

In addition to the above, the present invention also provides methods for manufacturing the pharmaceutical compositions of the present invention. Such methods of the present invention are disclosed hereinbelow. These methods include, in particular, the following methods:

11. Method of manufacturing the solid composition according to any one of items 1 to 9, which comprises the following steps in the specified order:
   (i) dry mixing some or all of the components of the composition;
   (ii) granulating the resulting mixture to obtain a granulate;
   (iii) admixing any remaining components of the composition to the granulate;
   (iv) compression of the resulting mixture to obtain a compressed tablet; and
   (v) optionally coating the resulting compressed tablet.

12. Method according to item 11, wherein the granulation step is performed by wet granulation or dry granulation.

13. Method according to item 11 or 12, wherein a part of the diluent, if present and/or a part of the disintegrant, if present, and part of or all of the glidant and lubricant, if present, is admixed to the granulate of step (ii).

Finally, the present invention provides uses of the pharmaceutical compositions according to the present invention. These uses are also described hereinbelow. They include, in particular, the following uses:

14. Solid pharmaceutical composition according to anyone of items 1 to 10 for use in a method of treating bacterial infections in a mammal.

15. Solid pharmaceutical composition for use according to item 14, wherein the mammal is a human.

16. Solid pharmaceutical composition for use according to item 14 or 15, wherein the bacterial infection is caused in particular by the bacterial species S. aureus, such infections being i.a. acute bacterial skin and skin-structure infection (ABSSSI) or bacterial infections associated with diabetic foot syndrome.

The present invention also pertains to methods for treating bacterial infections in a mammal in need thereof using the solid pharmaceutical compositions of the present invention, e.g. as specified in anyone of items 1 to 10 above. It specifically pertains to such methods, wherein the mammal is a human. In preferred embodiments of these methods of treatment of the present invention, the bacterial infection is caused by a bacterial species selected from S. aureus, including methicillin-resistant S. aureus.

DETAILED DESCRIPTION OF THE INVENTION

Definitions

Figure 1:
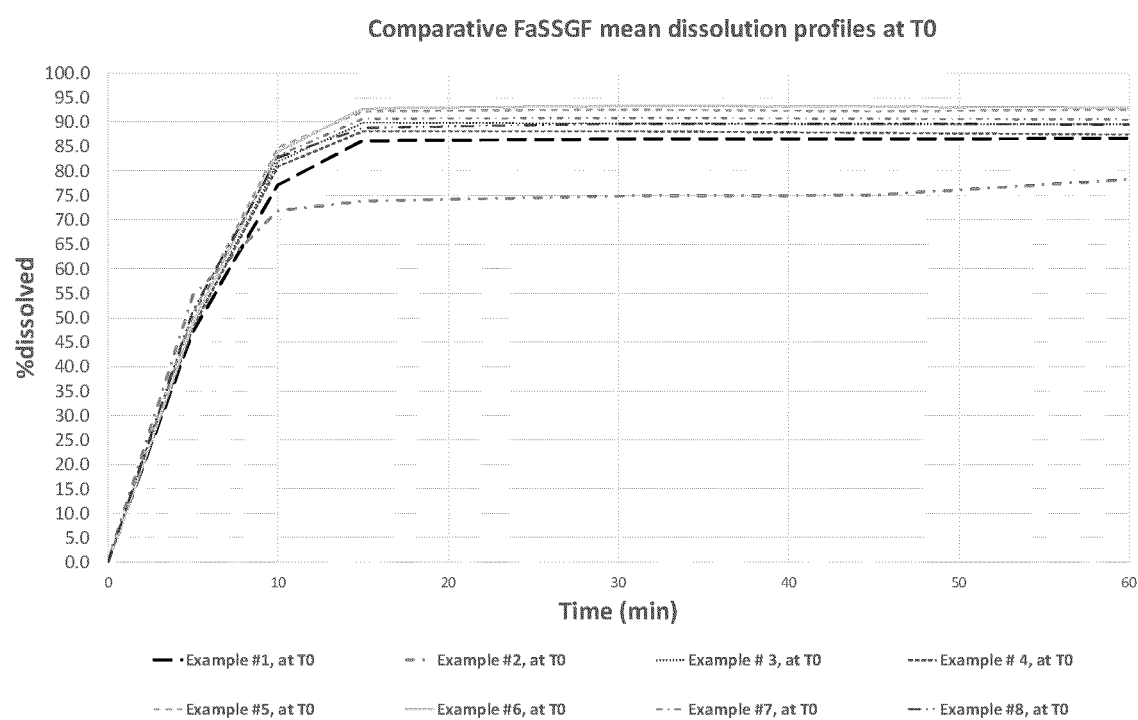
FIG. 1: In vitro dissolution profile of Examples 1 to 8 after manufacturing (T0)

The verbs "comprise" and "contain" introduce an open list that allows the additional presence of further components not included in said list. By contrast, the verb "consist of" introduces a closed list that does not permit the additional presence of further unmentioned components. Wherever the present application uses the verbs "comprise" or "contain", this is meant to include the option "consist of" as a preferred embodiment.

Unless the context dictates otherwise, the term "a" or "an" characterizes a substance or component but without restricting its number/amount. For instance, a reference to "a binder" is to be understood as a reference to a single binder or, alternatively, a combination of two or more binders.

The term "histidine compound" is used to characterize histidine itself as well as pharmaceutically acceptable salts thereof. Histidine or a pharmaceutically acceptable salt thereof may be used as the histidine compound in the racemic form, as the L-enantiomer, the D-enantiomer or any mixture thereof. It is preferred to use the L-enantiomer. Any reference to a histidine compound is also to be understood as a reference to histidine itself (only), which is the most preferred embodiment of the histidine compound.

The term "cellulosic material" characterizes a material that is a material containing at least 10 consecutive repeating units of the following general structure:

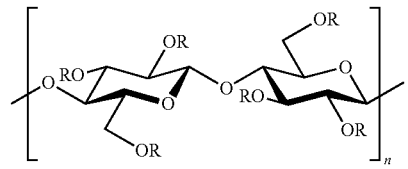

wherein n is 10 or more and each R is independently hydrogen or a substituent. In particular, each R in the repeating unit is independently selected from the group consisting of H, $C_{1-6}$ alkyl, hydroxy-$C_{1-6}$ alkyl, carboxy-$C_{1-6}$ alkyl, —(C=O)—$C_{1-6}$ alkyl.

The term "starch material" is used to characterize any material having at least 10 consecutive repeating units of amylose or amylopectin structure. Starch materials encompass also materials having at least 10 consecutive repeating units of amylose or amylopectin structure, wherein one or more substituents are attached to the amylose and/or amylopectin structural elements via hydroxyl group-derived oxygen atoms in the same manner as shown above for cellulose materials. Such starch materials may optionally be pregelatinized.

The term "polysaccharide", as used herein, refers to any material having at least 10 monosaccharide units linked by glycosidic bonds. The scope of the monosaccharides is not particularly restricted. Moreover, two or more different types of monosaccharides may simultaneously be present in a polysaccharide. Polysaccharides may be linear or branched.

The term "modified release agent" is used to characterize a group of materials, which are used in pharmaceutical industry to control, delay or prolong the release of an active pharmaceutical ingredient. Modified release agents include polymethacrylate (including methyl acrylate-methacrylic acid copolymers and/or methyl methacrylate-methacrylic acid copolymers), polyvinyl acetate phthalate, cellulose acetate phthalate, hypromellose acetate succinate, hypromellose phthalate, hypromellose (high molecular weight), methylcellulose (high molecular weight), microcrystalline wax, carbomers, guar gum, shellac, carrageenan, chitosan, glycerin monostearate, glyceryl behenate, glyceryl monooleate, glyceryl monostearate, glyceryl palmitostearate, polacrilin potassium, polycarbophil, polyethylene oxide (high molecular weight), alginic acid, sodium alginate and zein.

The term "dissolution stability" characterizes a formulation that exhibits a mean dissolution profile after short term storage in accelerated conditions, preferably after storage for 15 days at 40° C./75% RH in an open vial, that deviates, preferably slows down, by no more than 30%, preferably no more than 25% and more preferably no more than 20%, and even more preferably no more than 15% from the mean dissolution profile of the same formulation before storage. Deviations are to be determined at time points of 45 min and 60 min. A formulation is "dissolution stable" in the sense of the present invention only if there is less than 30%, preferably less than 25% and more preferably less than 20%, and even more preferably less than 15% deviation, preferably slow down, at all of these two time points. Relative deviation is to be calculated taking the dissolution values before storage as the standard. That is, relative deviation, can be calculated using the following equation:

Deviation, $$_{T=x}(\%) = 100\% \times |[Diss_{T=x}(\text{after storage}) - Diss_{T=x}(\text{before storage})]| / Diss_{T=x}(\text{before storage})$$

wherein $Diss_{T=x}$ characterizes the percentage of dissolved Afabicin at the time x.

The term "alkyl" refers to monovalent saturated hydrocarbon radicals of the general formula $C_nH_{2n+1}$. Alkyl residues may be linear or branched. Preferred alkyl groups have from 1 to 6 carbon atoms.

The term "alkoxy" refers to a monovalent radical of the general formula —O-alkyl, wherein the alkyl group is as defined above.

The present application refers to "components" of the pharmaceutical compositions of the present invention as any material that is present in the final product, including excipients and including also the pharmaceutically active ingredient. The term "components" also includes a tablet coating (if present) or a capsule shell (if present). "Excipients" are all components of the pharmaceutical composition that do not exercise a pharmaceutical effect on their own, i.e. all components other than the pharmaceutically active ingredient.

Unless specified otherwise, all absolute amount indications in the present application are given in mg. Unless specified otherwise, all relative amount indication are provided in weight % (wt %) based on the total weight of the pharmaceutical composition. If the pharmaceutical composition is in the form of a coated tablet, the weight of the coating is not included in said total weight. If the pharmaceutical composition is in the form of a capsule, the weight of the capsule shell is also excluded from said total weight. The weight of any liquid that may be temporarily present during wet granulation, but which is removed by subsequent drying procedures, is not included in said total weight.

Unless specified otherwise, all absolute amount indications, e.g., daily dosages, of the active substance Afabicin are based on the molecular weight of the free acid form. Hence, if a salt form of Afabicin is used, the specified absolute amounts need to be converted taking relative molecular weights into account. This can be done using the following equation (1):

$$m(\text{salt}) = m(\text{free acid}) * M(\text{salt}) / M(\text{free acid}) \quad (1)$$

wherein m specifies the absolute amount and M specifies the molecular weight of the respective form.

Unless specified otherwise, all relative amount indications, e.g. compositional ranges, of the active substance Afabicin are based on the molecular weight of the bis-ethanolamine salt of Afabicin (Afabicin Olamine). Hence, if a different salt form or the free acid form of Afabicin is used, the specified absolute amounts need to be converted taking relative molecular weights into account. This can be done using the following equation (2):

$$w(s2) = 100 * w(s1) * M(s2) / (M(s1) * (100 + w(s1) * (M(s2) - M(s1)) / M(s1))) \quad (2)$$

wherein w(s2) is the relative amount of a second salt form or the free acid form (in wt % based on the total weight of the composition containing this salt form); w(s1) is the relative amount of the bis-ethanolamine salt form (in wt % based on the total weight of the composition containing the bis-ethanolamine salt form; M(s2) is the molecular weight of said second salt form or the free acid form; and M(s1) is the molecular weight of the bis-ethanolamine salt form.

Indications in the present application that the pharmaceutical compositions of the present invention are "free" of a particular substance, indications that no substance of this type is present, as well as statements that said substance is absent, omitted, or the like, are to be understood such that the relative amount of said substance in the pharmaceutical composition is less than 0.1 wt % and preferably less than 0.01 wt %. According to a particularly preferred embodiment, said substance is completely absent or present only in such a small amount that it cannot be detected based on analytical techniques available at the filing date. According to another embodiment, the pharmaceutical composition contains the respective substance in such a small amount that it has no measurable impact on the dissolution characteristics of the active ingredient Afabicin.

Indications of relative amounts of components by means of ranges are to be understood such that, in case of "comprising" language, any amount within the specified range can be present with the proviso that the total amount of mentioned components must be 100 wt % or less to allow for the optional presence of additional unmentioned components. In case of "consisting of" language, any amount within the specified range can be present with the provision that the total amount of mentioned components must be 100 wt %. In this connection, the term "mentioned component" refers to any components, for which a relative amount is specified in the same technical context.

Some of the excipients mentioned hereinbelow may have two or more functions. For instance, poloxamer may be used as a surfactant but it may also function as a binder component. It is perfectly in agreement with the present invention to make use of such components in order to benefit from two or more of the functions of the respective component. If such a component having two or more functions is employed, it is of course possible to reduce the amount of, or to completely omit any other component having one of these functions. As regards amount indications, the following is to be considered:

The histidine compound is to be considered only in its function as agent for improving dissolution characteristics, irrespective whether it might also exercise any other function. For instance, if the formulation contains the diluent mannitol and/or isomalt in addition to the histidine compound, the diluent amount is the same as the mannitol and/or isomalt amount, which means that the amount of histidine compound is not to be counted for the diluent irrespective whether the histidine compound exercises a diluent function or not.

Amount indications provided below are to be understood such that such a multifunctional component is to be taken into account for each of its functions, which it can exercise in the pharmaceutical composition. If, for instance, poloxamer is present in an amount of 5 wt %, this component should be counted as 5 wt % surfactant and, additionally, 5 wt % of binder.

It is possible and in agreement with the present invention that a multifunctional component is used in an amount that is in agreement with the amount indication given for one type of component, but which is higher than the amount indication(s) given for one or more other types of components. In this case, only the fraction of the component in accordance with upper limit(s) of this/these lower amount indication(s) is deemed to be present for assessing conformity with the lower amount indications in the present invention, whereas the full amount is considered for assessing conformity with the higher amount indication. For instance, if 50 wt % starch is used, which may function as a diluent and also as a binder, the question arises whether this amount is in accordance with the amount indications specified below. According to one embodiment described below, the diluent may be present in an amount of 50-75 wt % and the binder may be present in an amount of 4-7 wt %. Using 50 wt % starch is in agreement with this embodiment: for the binder function, it is deemed that 7 wt % of the starch functions as a binder while the entire amount of 50 wt % is to be considered for the diluent function.

It is also possible and in agreement with the present invention that a multifunctional component is used in an amount that is in agreement with the amount indication given for one type of component, but lower than the amount indication(s) given for one or more other types of components. In this case, additional components having the same function must be used in sufficient amounts to comply with the amount indications specified for these other types of components. For example, if, by analogy to the above example, an amount of 7 wt % starch is present, this will be in agreement with the binder amount specified for the above-mentioned embodiment. In order to comply also with the amount specification for the diluent component, at least 43 wt % of another diluent must be used in addition to the starch component.

If there is any doubt about the functions performed by a particular component, the information provided hereinbelow shall be considered as decisive. In the absence of information hereinbelow, this information may be supplemented by the information contained in "Handbook of Pharmaceutical Excipients" by P. J. Sheskey, Pharmaceutical Press, $8^{th}$ Edition 2017.

Overview

The present invention is based on the surprising finding that the release characteristics of Afabicin-containing formulations can be significantly improved by incorporating histidine compounds into the formulations.

Histidine is a well-known pharmaceutical ingredient commonly used in protein freeze-dried formulations for parenteral administration and acts as a buffer (see Excipient Development for Pharmaceutical, Biotechnology, and Drug Delivery Systems, ed Ashok Katdare, Mahesh Chaubal, CRC Press, 2006, p 299 to 300). Histidine has been shown to protect a monoclonal antibody in both the liquid and lyophilised state against heat stress (see Arakawa et al., Biotechnology Applications of Amino Acids in Protein Purification and Formulations. Amino Acids. 33, 587-605).

Without wishing to be bound to this theory, it is speculated that the histidine compound is advantageous because it stabilizes Afabicin through molecular interactions. In particular, it is possible in this manner to provide formulations that readily release Afabicin without disintegration problems. This general inventive concept can be implemented with any kind of solid dosage form, including in particular tablets and capsules. The benefits of the present invention are most prominent in tablets and especially in tablets having an internal phase and an external phase. It is particularly advantageous to employ the specified excipient materials for manufacturing such a tablet having an internal phase comprising Afabicin, as well as an external phase not comprising Afabicin. In this case, it is preferred to provide the histidine compound at least in the internal phase.

Even better results can be accomplished if histidine itself is incorporated into the formulation. It is therefore a preferred embodiment of the present invention to incorporate histidine. The present invention further provides solid pharmaceutical compositions containing one or more of a range of excipient materials that are well suited for manufacturing Afabicin-containing solid dosage forms that exhibit excellent dissolution and stability characteristics. In preferred embodiments, the present invention also provides solid pharmaceutical compositions characterized by the absence of other excipient materials as specified in the next section as an alternative approach for improving dissolution and stability characteristics.

Substances Preferably to be Avoided

The pharmaceutical compositions of the present invention are preferably free of cellulosic materials. This means especially that none of the following materials is present: Microcrystalline cellulose, silicified microcrystalline cellulose, hydroxypropyl methyl cellulose, hydroxypropyl cellulose, hydroxyethyl cellulose, hydroxyethylmethyl cellulose, methyl cellulose, carboxymethyl cellulose and salts thereof, but also any other polymeric substance based on cellulose repeating units as defined above.

As a more preferred embodiment the pharmaceutical compositions of the present invention are additionally free of starch materials. In particular, the pharmaceutical compositions of the invention are free pregelatinized starch. According to yet another preferred embodiment of the present invention, the pharmaceutical compositions of the invention do not contain any polysaccharide material at all.

The above general rules for preferred embodiments without cellulose materials and/or starch materials or even without polysaccharides in general apply irrespective of the intended function of the component and the localization of the component within the solid dosage form. For instance, in a tablet containing an internal phase an external phase as well as a coating, there is no cellulosic material in the internal phase, no cellulosic material in the external phase and no cellulosic material in the coating.

It is also preferred not to include modified release agents into the pharmaceutical composition. This applies equally to a coating thereof, if present.

Active Substance

Unless the context dictates otherwise, the term "Afabicin" is used herein to characterize the chemical compound shown above, as well as any pharmaceutically acceptable salt form thereof.

Afabicin can be used in the form of the free acid and/or it can be used in a pharmaceutically acceptable salt form.

The free acid form of Afabicin has been attributed the following CAS RN 1518800-35-5. The most advantageous salt form presently known is the bis-ethanolamine salt, which is shown below.

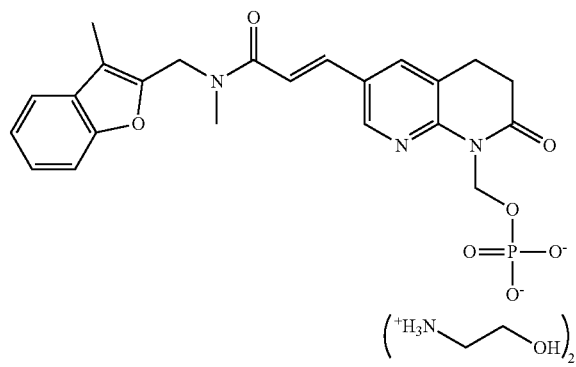

Afabicin, under this bis-ethanolamine salt form, is also called Afabicin Olamine and its CAS RN is 1518800-36-6.

A mixture of the free acid form and the bis-ethanolamine salt of Afabicin is also advantageously used. According to a particularly preferred embodiment of the present application, all references to Afabicin are to be understood as references to the Afabicin bis-ethanolamine salt optionally in combination with Afabicin in the free acid form. In the most preferred embodiment, a combination of Afabicin bis-ethanolamine salt with Afabicin in the free acid form is used, wherein the molar ratio of free acid to bis-ethanolamine salt is in the range of from 0.7 to 0.9 and even more preferably from 0.75 to 0.85.

Apart from the above-mentioned particularly preferred embodiment, it is also possible but less preferable to use alternative salt forms of Afabicin, such as the bis-potassium salt or a monobasic dialkylammonium salt wherein the alkyl group is selected from methyl and ethyl groups. In principle, the type of salt form is not particularly limited and it is therefore possible to use any pharmaceutically acceptable salt form of Afabicin, including but not limited to the salts disclosed in WO 2013/190384.

The above-mentioned forms including the free acid form and less preferred salt forms may of course be used in combination. Amount indications provided for Afabicin refer to the amount of the free acid form. If a salt of Afabicin is used, the amount must be correspondingly adjusted taking the higher molecular weight of the Afabicin salt into account. This is most easily done for an absolute amount indication in mg. The adjusted value may then be converted into a relative amount, if needed.

Afabicin may be present in the pharmaceutical composition of the present invention in an amount of 20 mg to 480 mg, preferably from 40 mg to 240 mg and most preferably in a weight of 120 mg or 240 mg.

The relevant amount of Afabicin salt in the compositions of the invention may range from 10 wt % to 90 wt %, preferably from 30 wt % to 85 wt % and most preferably from 40 wt % to 60 wt %. As indicated above, such relative amount indications are applicable to Afabicin Olamine. If another Afabicin salt or the free acid form of Afabicin is used, the relative amount will have to be converted taking the molecular weight of Afabicin Olamine and of the Afabicin form of interest into account. A suitable formula for this calculation is provided in the definitions section above.

It is also possible in accordance with the present invention to combine the Afabicin active substance with another active drug substance. Drug substances suitable for such combinations are described in paragraphs [0132] to [0140] of WO 2013/190384 A, which is herewith incorporated by reference.

Histidine Compound

The histidine compound is used as an agent allowing composition disintegration and Afabicin release. In a preferred embodiment, the histidine compound is histidine itself. Instead of the histidine compound in the free form, it is also possible to use a pharmaceutically acceptable salt thereof, such as the citrate salt. Histidine or a pharmaceutically acceptable salt thereof may be used in the racemic form, as the L-enantiomer, the D-enantiomer or any mixture thereof. It is preferred to use the L-enantiomer. Another possibility in accordance with the present invention is to use a combination of two or more histidine compounds, e.g. a combination of histidine and a histidine salt. It is also possible to use the histidine compound together with one or more further compounds exhibiting molecular interaction with Afabicin or Afabicin salt.

If the histidine compound is used as the sole agent of this type, it may be present in a molar ratio relative to Afabicin or Afabicin salt of (histidine compound)/(Afabicin (salt))=0.5 to 5, preferably 0.6 to 4.5, 0.7 to 4, 0.75 to 4, or 0.8 to 3.5, or 1 to 3, or more preferably 1 to 2. If the histidine compound is used together with another stabilizing agent exhibiting molecular interaction with Afabicin or Afabicin salt, it may be present together with the other stabilizing agent in a molar ratio relative to Afabicin or Afabicin salt of (histidine compound+other stabilizing agent)/(Afabicin (salt))=0.5 to 10, preferably 0.6 to 9, 0.7 to 8, 0.75 to 8, or 0.8 to 7, or 1 to 6, more preferably to 1 to 3.

If the relative amount of the Afabicin or Afabicin salt and of the histidine compound is known, the molar ratio may be calculated relying on the following formula, which is shown in an exemplary fashion for an Afabicin salt. An analogous formula applies if the free form of Afabicin is used:

Molar ratio(histidine compound/Afabicin salt)=(% wt(histidine compound)/$M$(histidine compound))/(% wt(afabicin salt)/$M$(afacibin salt))

wherein M (histidine compound) is the molecular weight of histidine compound; M (Afabicin salt) is the molecular weight of Afabicin salt (or Afabicin itself, if the free form is used instead of a salt)

Binder

A binder is advantageously used for increasing the particle size of active ingredient alone or with excipients and improve its handling properties. There is no particular limitation on the binder material that can be employed in the present invention. According to a preferred embodiment, no cellulosic material is used. According to another preferred embodiment, no starch material is used.

Suitable binder materials include povidone (polyvinylpyrrolidone), copovidone (Poly(1-vinylpyrrolidone-co-vinyl acetate)), hydroxy propyl cellulose, hydroxyl propyl methyl cellulose, hydroxyethyl cellulose, methyl cellulose, microcrystalline cellulose, poloxamer (a block copolymer with a first poly(ethylene oxide) block, a second and central poly(propylene oxide) block and a third poly(ethylene oxide) block), polyethylene glycol, magnesium aluminosilicate, gelatin, acacia, alginic acid, carbomer (e.g. carbopol), carrageenan, dextrin, dextrates (a purified mixture of saccharides developed from the controlled enzymatic hydrolysis of starch), dextrose, polydextrose, guar gum, hydrogenated vegetable oil, liquid glucose, maltose, sucrose, lactose, wax, maltodextrin, starch (pregelatinized and plain), hydroxypropyl starch, glyceryl behenate, glyceryl palmitostearate, polyethylene oxide, sodium alginate, ethycellulose, cellulose acetate phthalate, polymethacrylate, carboxymethyl cellulose sodium, polycarbophil, chitosan and mixtures thereof.

The use of povidone and copovidone is preferred.

The binder may be present in a relative amount of from 0.5 wt % to 15 wt %, preferably from 2 wt % to 10 wt % e.g. 2 wt % to 8 wt % and more preferably 3 wt % to 8 wt % e.g. 3 wt % to 6 wt %.

Diluent

Diluents are optionally but advantageously used for increasing the bulk of the pharmaceutical composition and for facilitating handling of the composition. There is no particular limitation on the diluent material that can be employed in the present invention. Similar to the situation described for the binder above, it is preferred not to use a cellulosic material and/or not to use a starch material and/or not to use a modified release agent.

Suitable diluent materials include mannitol, isomalt, lactose (including anhydrous or monohydrate forms), calcium phosphate (including dibasic and tribasic calcium phosphate), calcium carbonate, magnesium carbonate, magnesium oxide, calcium sulfate, sucrose, fructose, maltose, xylitol, sorbitol, maltitol, lactitol, trehalose, aluminium silicate, dextrose, cyclodextrin (native or modified), starch (pregelatinized or plain), maltodextrin, cellulose (microcrystalline, silicified microcrystalline), glucose, dextrin, dextrates (a purified mixture of saccharides developed from the controlled enzymatic hydrolysis of starch), dextrose, polydextrose, ammonium alginate, glyceryl behenate, glyceryl palmitostearate, sodium alginate, ethycellulose, cellulose acetate, cellulose acetate phthalate, polymethacrylate, chitosan and mixtures thereof.

The use of mannitol, xylitol, sorbitol and/or isomalt is preferred, and most preferably mannitol and/or isomalt.

The diluent, if present, may be present in a relative amount that is not particularly restricted. Suitable amounts may range from 2 wt % to 85 wt %, preferably from 8 wt % to 80 wt % and more preferably 10 wt % to 30 wt %.

Surfactant

In an embodiment the composition comprises a surfactant. A surfactant may advantageously be used for assisting wettability of the tablet and of the active ingredient. The surfactant is an optional but preferred component. There is no particular limitation on the surfactant material that can be employed in the present invention. Similar to the situation described for the binder above, it is preferred not to use a cellulosic material and/or not to use a starch material and/or not to use a modified release agent.

Suitable surfactant materials include sodium lauryl sulfate, poloxamer, sodium docusate, sodium deoxycholate, sorbitan esters, polyethylene oxide, polysorbate 20, polysorbate 40, polysorbate 60, polysorbate 80 (ethoxylated sorbitan esterified with fatty acids wherein the number indicates the number of repeating units of polyethylene glycol), sucrose esters of fatty acid, tyloxapol, lecithin and mixtures thereof.

The use of sodium lauryl sulfate is preferred.

The surfactant may be present in a relative amount that is not particularly restricted. Suitable amounts may range from 0 wt % or more to 7 wt %, preferably from 0.1 wt % to 6.5 wt % and more preferably 1 wt % to 6 wt %. In one specific embodiment, a surfactant is present, preferably in an amount range as specified above, and the molar ratio of Afabicin or Afabicin salt relative to histidine compound (and other stabilizing agent, if present) is set to fall within one of the ranges described hereinabove. For instance, a surfactant may be present in an amount of 0.1 wt % to 6.5 wt % while the above-mentioned molar ratio may be greater than 0.5 and may for example be 0.6 to 4.5 if no other stabilizing agent is present or 0.6 to 9 if another stabilizing agent is present.

Disintegrant

A disintegrant is advantageously used for accelerating disintegration of the pharmaceutical composition to thereby assist in dissolution of the active ingredient. There is no particular limitation on the disintegrant material that can be employed in the present invention. Similar to the situation described for the binder above, it is preferred not to use a cellulosic material and/or not to use a starch material and/or not to use a modified release agent.

Suitable disintegrant materials include crospovidone, sodium starch glycolate, sodium croscarmellose, magnesium aluminosilicate, colloidal silicon dioxide, sodium alginate, calcium alginate, pregelatinized starch, microcrystalline cellulose, methylcellulose, hydroxypropyl cellulose, calcium carboxymethylcellulose, sodium carboxymethylcellulose, alginic acid, guar gum, homo- and copolymers of (meth)acrylic acid and salts thereof such as polacrillin potassium, and mixtures thereof.

The use of crospovidone is preferred

The disintegrant may be present in a relative amount that is not particularly restricted. Suitable amounts may range from 0 wt % or more to 20 wt %, preferably from 1 wt % to 15 wt % and more preferably 2 wt % to 10 wt %.

Glidant

A glidant is advantageously used for improving flowability of the pharmaceutical composition to thereby improve its handling properties. The glidant is an optional but preferred component. There is no particular limitation on the glidant material that can be employed in the present invention. Similar to the situation described for the binder above, it is preferred not to use a cellulosic material and/or not to use a starch material and/or not to use a modified release agent.

Suitable glidant materials include colloidal silica dioxide, magnesium oxide, magnesium silicate, calcium silicate, tribasic calcium phosphate, talc, and mixtures thereof.

The use of colloidal silica dioxide is preferred.

The glidant may be present in a relative amount that is not particularly restricted. Suitable amounts may range from 0 wt % or more to 5 wt %, preferably from 0.1 wt % to 4 wt % and more preferably 0.2 wt % to 1 wt %.

Lubricant

Lubricants are advantageously used to facilitate tableting, in particular by preventing sticking of the tablets to the tablet punch. The lubricant is an optional but preferred component. There is no particular limitation on the lubricant material that can be employed in the present invention. Similar to the situation described for the binder above, it is preferred not to use a cellulosic material and/or not to use a starch material and/or not to use a modified release agent.

Suitable lubricant materials include magnesium stearate, sodium stearyl fumarate, talc, stearic acid, leucine, poloxamer, polyethylene glycol, glyceryl behenate, glycerin monostearate, magnesium lauryl sulfate, sucrose esters of fatty acids, calcium stearate, aluminum stearate, hydrogenated castor oil, hydrogenated vegetable oil, mineral oil, sodium benzoate, zinc stearate, palmitic acid, carnauba wax, magnesium lauryl sulfate, sodium lauryl sulfate, polyoxyethylene monostearates, calcium silicate, and mixtures thereof.

The use of a lubricant selected from magnesium stearate and sodium stearyl fumarate, and combinations thereof is preferred The lubricant may be present in a relative amount that is not particularly restricted. Suitable amounts may range from 0 wt % or more to 7 wt %, preferably from 0.1 wt % to 5 wt % e.g. 0.1 wt % to 4 wt % and more preferably 0.25 wt % to 4 wt % e.g. 0.5 wt % to 3.5 wt %.

Other Types of Excipients

The composition of the present invention may contain further excipients that are commonly used in the art. Such further excipients may include plasticizer, film forming agent, colorant, anti-tacking agent and/or pigment for coating the compositions of the present invention. Further types of excipients, which may be present, include buffer agents, flavoring agents, sweeteners, antioxidants and/or absorption accelerators. Similar to the situation described for the binder above, it is preferred not to use a cellulosic material and/or not to use a starch material and/or not to use a modified release agent.

Relative amounts of such excipients are not particularly limited. They may be determined by the skilled person based on common general knowledge and routine procedures.

Film forming agents are advantageously used for providing the tablets of the invention with a coherent coating. Suitable film forming agents include isomalt, polyvinyl alcohol, polyethylene glycol, maltodextrin, sucrose, xylitol, maltitol. Enteric coating agents such as materials selected from the group consisting of methyl acrylate-methacrylic acid copolymers, polyvinyl acetate phthalate (PVAP), methyl methacrylate-methacrylic acid copolymers, shellac, sodium alginate and zein may be used, but this is not preferred. Similar to the situation described for the binder above, it is preferred not to use a cellulosic material and/or not to use a starch material. It is preferred to use a combination of film forming agents comprising polyvinyl alcohol and one or more second agents selected from isomalt, sucrose, xylitol, and maltitol.

Suitable plasticizers include sorbitol, triacetin, poloxamer, polyethylene glycol, glycerin, propylene glycol, polyethylene glycol monomethyl ether, acetyl tributyl citrate, acetyl triethyl citrate, castor oil, glyceryl monostearate, diacetylated monoglyerides, dibutyl sebacate, diethyl phthalate, triethyl citrate, and tributyl citrate.

Tablet

The pharmaceutical compositions of the invention are preferably in the form of tablets. Tablets may be single layer monolithic tablets, they may be of a layered structure having two or more layers or they may have a structure with an internal phase (obtained by a granulation step) and an external phase. The variant with an internal and external phase is particularly preferred. In this variant, it is also particularly preferred that the active drug substance Afabicin is present solely in the internal phase. In this variant, it is furthermore particularly preferred that at least some, e.g. more than 50% and preferably more than 80%, of the histidine compound is also present in the internal phase. It is as well preferred that at least some, e.g. more than 50% and preferably more than 55%, of the disintegrant is also present in the internal phase. If the tablet has an internal phase and an external phase, it is preferred that the weight ratio of the internal phase to the external phase is 50:50 or higher and more preferably in the range of from 80:20 to 95:5.

If the tablet is a single layer tablet, the above amount indications apply without restrictions. In case of a two layer tablet, some of the components may be separated from each other by incorporating them into separate layers. In case of tablets having two or more layers, it is preferred that that at least some, e.g. more than 50% and preferably more than 80%, of the histidine compound is present in the same layer as Afabicin. In case of tablets having two or more layers, it is as well preferred that at least some, e.g. more than 50% and preferably more than 55%, of the disintegrant is also present in the same layer than Afabicin. Apart from that, there are no particular restrictions regarding the allocation of excipients to the different layers. In case of a multilayer tablet with three or more layers, it is preferred to incorporate the active substance Afabicin and ideally also the histidine compound solely into an outer layer. For this preferred embodiment, the above restrictions apply together with those provided below for the tablet with internal and external phase (such that indications for the internal phase apply to at least one of the inner layer(s) whereas indications for the external phase apply to the outer layers and any inner layer, which may be present in addition to the Afabicin-containing layer).

Internal Phase

The internal phase, if present, contains preferably the following components:
Afabicin or Afabicin salt (50-100 wt. %, preferably 100 wt %, of the total amount of Afabicin or Afabicin salt);
Histidine compound (50-100 wt. %, preferably 100 wt. %, of the total amount of histidine compound);
Binder (50-100 wt. %, preferably 100 wt %, of the total amount of binder);
Optionally Diluent (0-100 wt. %, preferably 0-20 wt. %, of the total amount of diluent); these amounts do not include histidine compound amount describe above;
Optionally surfactant (50-100 wt. %, preferably 100 wt %, of the total amount of surfactant);
Optionally disintegrant (40-100 wt. %, preferably 60-100 wt. %, of the total amount of disintegrant);
Optionally glidant (0-100 wt. %, preferably 0-50 wt. % of the total amount of glidant); and
Optionally lubricant (0-100 wt. %, preferably 0-50 wt. % of the total amount of lubricant).

Additional components such as release rate modifiers, colorants, buffer agents, flavoring agents and/or sweeteners may also be present in the internal phase.

External Phase

The external phase, if present, contains preferably the following components:
Afabicin or Afabicin salt (0-50 wt. %, preferably 0 wt %, of the total amount of Afabicin or Afabicin salt);
Histidine compound (0-50 wt. %, preferably 0 wt. %, of the total amount of histidine compound);
Binder (0-50 wt. %, preferably 0 wt %, of the total amount of binder);
Optionally Diluent, (0-100 wt. %, preferably 80-100 wt. %, of the total amount of diluent); these amounts do not include histidine compound amount describe above;
Optionally surfactant (0-50 wt. %, preferably 0 wt %, of the total amount of surfactant);
Optionally disintegrant (0-60 wt. %, preferably 0-40 wt. %, of the total amount of disintegrant);
Optionally glidant (0-100 wt. %, preferably 50-100 wt. % of the total amount of glidant); and
Optionally lubricant (0-100 wt. %, preferably 50-100 wt. % of the total amount of lubricant).

The above wt. % indications are calculated with respect to the total weight of the respective compound in the tablet being 100 wt. %. For instance, it is in accordance with the above indications to prepare a tablet with 240 mg Afabicin having 200 mg Afabicin in the internal phase and 40 mg of Afabicin in the external phase. This distribution corresponds to 83 wt. % of Afabicin in the internal phase and 17 wt. % in the external phase. It is therefore in accordance with the ranges specified hereinabove.

Additional components such as release rate modifiers, buffer agents, colorants, pigments, flavoring agents and/or sweeteners may also be present in the external phase.

Coating

The tablet of the invention may optionally be provided with a coating, irrespective whether it is a single layer tablet, a multilayer tablet or a tablet with an internal phase and an external phase. Such a coating may serve aesthetic purposes and it may also facilitate labelling, handling and swallowing the tablet and/or have a protective effect.

Suitable materials for the coating are not particularly restricted. Typically, coatings include a film forming agent as described above, wherein it is preferred to use the film forming agent combinations described above as being preferred or more preferred. Additional components such as plasticizers, colorants and/or pigments, anti-caking agent, may also be present in the coating.

Capsule

In another embodiment, the pharmaceutical composition may be in the form of a capsule. In this embodiment, the components of the present application include preferably the materials mentioned above:

Afabicin;
Histidine compound;
Optionally binder;
Optionally Diluent;
Optionally surfactant but preferred;
Optionally disintegrant but preferred;
Optionally lubricant and
Optionally glidant, wherein the relative amounts of these components are preferably the same as specified above. The components of the capsule composition may be provided and introduced into the capsule shell in powder form or in granulated form.

The capsule shell may be made from gelatin or any other material, such as polyvinyl alcohol and polyvinyl alcohol-based polymers, alginate or pullulan. Similar to the situation described for the binder above, it is preferred not to use a capsule containing a starch material and/or a modified release agent. However, different from the situation above, a cellulosic material should be completely avoided as a capsule material. The use of gelatin is preferred. There is no particular limitation regarding the capsule size and/or amount of the composition to be filled into the capsule shell.

Method of Manufacturing

The tablet of the present invention can be manufactured using conventional equipment and techniques. Such methods of manufacturing may comprise in particular a first step of dry mixing and granulating some or all of the components of the composition, followed by a step of admixing any remaining components of the composition followed by compression of the resulting mixture and, finally, followed by an optional coating step. In this method, the granulation type may be selected from wet granulation, dry granulation, and melt granulation. In a further method of the present invention, the granulation step may be completely omitted (i.e. direct compression). After granulation but before compression into a tablet, the resulting granulate is preferably screened and/or milled to obtain the desired particle size. In case of wet granulation, the granulate is furthermore dried before or after the screening and/or milling. A preferred granulation liquid to be used for wet granulation is water which may optionally contain binder.

Among the components of the composition of the present invention, it is preferred to admix part or all of the glidant, lubricant, disintegrant and diluent after the granulation step while granulating the remaining components (excluding, of course, the components used for the optional coating).

The tablet with an internal phase and an external phase may in principle be manufactured in the same manner as described above, but with the following modifications: the compositions for the internal phase and external phase are separately prepared and the composition for the internal phase is granulated. Then, the granulated composition for the internal phase is blended with the composition for the external phase and the resulting blend is compressed in a tableting machine to obtain the final tablet with internal and external phase.

The capsules of the present invention can be manufactured by dry mixing some or all of the components of the composition, optionally granulating the mixture, admixing any remaining components and finally introducing the resulting composition into a capsule shell.

Uses

The pharmaceutical compositions of the present invention are suitable for use in the treatment of bacterial infections in a patient in need thereof. In particular, they are suitable for the treatment of infections caused in particular by *S. aureus*, including methicillin-resistant *S. aureus* such as acute bacterial skin and skin structure infection (ABSSSI), or diabetic foot-associated bacterial infections.

Treatment of the patient by the pharmaceutical compositions of the present invention is by means of oral administration. Typically, a single unit dose of the pharmaceutical composition of the present invention is administered at least once a day and administration two times a day is preferred. The daily dosage is determined by the physician taking severity of the infection, gender, weight, age and general condition of the patient into account. Typical daily dosages range for human from 120 to 480 mg. Typical daily dose is 120 or 240 mg twice a day, for a total of 240 to 480 mg per day. Hence, the pharmaceutical composition of the present invention preferably has a unit dose strength of 120 mg or 240 mg of active pharmaceutical ingredient (calculated as Afabicin; e.g. if Afabicin Olamine is used, the preferred unit dose strength in terms of the total weight of Afabicin Olamine is 150 mg or 300 mg, respectively).

The patient to be treated is a mammal, typically selected from human, companion animal and food animal and preferably a human.

PREFERRED EMBODIMENTS

It is particularly preferred to work the present invention by combining two or more of the embodiments that are characterized in the above description or appended claims as being preferred. It is equally preferred to combine embodiments of differing degrees of preference, e.g. to combine a preferred binder material with a particularly preferred tablet type.

The following preferred embodiments are important and therefore specifically mentioned:

(A) According to one group of preferred embodiments, two or more components of the pharmaceutical composition containing Afabicin and the histidine compound are selected from the lists of preferred component materials. That is, it is preferable if, for two or more of the following component types (A1) to (A6), the respective component is selected from the following lists of preferred components:
- (A1) a binder selected from povidone and copovidone and combinations thereof;
- (A2) a diluent selected from mannitol, xylitol, sorbitol, isomalt and combinations thereof and most preferably mannitol, isomalt and combinations thereof;
- (A3) sodium lauryl sulfate as surfactant;
- (A4) crospovidone as disintegrant;
- (A5) colloidal silica dioxide as glidant; and
- (A6) a lubricant selected from magnesium stearate and sodium stearyl fumarate and combinations thereof.

It is even more preferred if all of the above-mentioned component types that are present are selected from the above lists of preferred components.

(B) Particularly preferred embodiments of the present invention relate to solid pharmaceutical compositions that are in the form of an optionally coated tablet having an internal phase and an external phase, (B1) wherein the internal phase comprises
- 40 to 60 wt % Afabicin or Afabicin salt (calculated as Afabicin Olamine),
- Molar ratio of 1 to 2 of histidine compound relative to Afabicin or Afabicin salt,
- 0 to 10 wt % diluent, (these amounts do not include histidine compound describe above)
- 3 to 6 wt. % binder,
- 1 to 6 wt % surfactant, and
- 1.2 to 10 wt. % disintegrating agent,
- 0 to 0.5 wt % glidant,
- 0 to 1.75 wt. % lubricant, and/or (B2) wherein the external phase comprises
- 8 to 50 wt % diluent, (these amounts do not include histidine compound describe above)
- 0 to 4 wt % disintegrant,
- 0.1 to 1 wt % glidant, and
- 0.25 to 3.5 wt % lubricant, and/or (B3) wherein the tablet is coated with a coating comprising
- 0.5 to 6 wt % film forming agents and
- 0.1 to 1.5 wt. % plasticizer.

All of the above relative amount indications are based on the total weight of the tablet.

A particularly preferred formulation is an uncoated tablet characterized by the components and relative amounts thereof as specified below.

Internal phase:
- 55 to 59 wt % Afabicin Olamine,
- 19 to 23 wt. % of histidine
- 5.75 to 7.75 wt. % binder,
- 5.0 to 7.0 wt % surfactant, and
- 2.0 to 4.0 wt. % disintegrating agent, and external phase:
- 1.0 to 3.0 wt % disintegrant,
- 0.1 to 0.9 wt % glidant, and
- 2.0 to 5.0 wt % lubricant.

This tablet is preferably manufactured by mixing and wet granulation of the components of the internal phase, followed by admixture of the components of the external phase, followed by compression.

A more specific preferred embodiment is characterized by the following composition and amounts (indications in mg/tablet):

Internal Phase:
- Afabicin Olamine: 300.41 (corresponding to 240.00 mg of Afabicin)
- Povidone: 34.65
- L-Histidine: 112.65
- Sodium Lauryl Sulfate: 30.00
- Crospovidone: 15.75

External Phase:
- Crospovidone: 10.51
- Colloidal Silica: 2.40
- Magnesium Stearate: 18.00

Even more preferred is of course a tablet, wherein the features of group (B1) and of group (B2) are fulfilled. Particularly preferred is a tablet wherein the features of groups (B1), (B2) and (B3) are simultaneously fulfilled.

(C) According to another particularly preferred embodiment, the pharmaceutical composition is in the form of an uncoated tablet, or it is in the form of a coated tablet wherein the coating comprises polyvinyl alcohol and a second film forming agent, or it is in the form of a gelatin capsule.

(D) According to an even more preferred embodiment, the above-mentioned tablet, especially the tablet according to any one of the above-mentioned embodiments (A), (B) or (C), comprises Afabicin in the form of the bis ethanolamine salt.

Most preferred is a tablet, wherein the preferred features of groups (A), (B), (C) and (D) are simultaneously fulfilled. Ideally this includes a combination of all preferred subgroups including (A1) to (A6) and (B1) to (B3).

Yet another particularly preferred formulation is an uncoated tablet characterized by the components and relative amounts thereof as specified below.

Internal Phase:
- 48 to 52 wt % Afabicin Olamine,
- 17 to 21 wt. % of histidine
- 4.75 to 6.75 wt. % binder,
- 4.0 to 6.0 wt % surfactant, and
- 1.6 to 3.6 wt. % disintegrating agent, and external phase:
- 10.5 to 14.5 wt % diluent, (this amount does not include histidine compound describe above)
- 0.75 to 2.75 wt % disintegrant,
- 0.1 to 0.7 wt % glidant, and
- 2.0 to 4.0 wt % lubricant.

This tablet is preferably manufactured by mixing and wet granulation of the components of the internal phase, followed by admixture of the components of the external phase, followed by compression.

A particularly advantageous formulation according to the preferred embodiments described above is characterized by the presence of the following specific components:
- povidone as the binder,
- sodium lauryl sulfate as the surfactant,
- crospovidone as the disintegrant,
- isomalt or mannitol as the diluent other than histidine,
- colloidal silica as the glidant, and
- magnesium stearate as the lubricant.

Implementing the use of these particularly preferred specific components with the particularly preferred relative amounts thereof yields the following particularly preferred formulation:

Internal phase:
- 48 to 52 wt % Afabicin Olamine,
- 17 to 21 wt. % of histidine
- 4.75 to 6.75 wt. % povidone,
- 4.0 to 6.0 wt % sodium lauryl sulfate, and
- 1.6 to 3.6 wt. % crospovidone, and external phase:
- 10.5 to 14.5 wt % isomalt and/or mannitol,
- 0.75 to 2.75 wt % crospovidone,
- 0.1 to 0.7 wt % colloidal silica, and 2.0 to 4.0 wt % magnesium stearate.

This tablet is preferably manufactured by mixing and wet granulation of the components of the internal phase, followed by admixture of the components of the external phase, followed by compression.

A particularly preferred embodiment is characterized by the following composition and amounts (indications in mg/tablet):

Internal Phase:
Afabicin Olamine: 300.41 (corresponding to 240.00 mg of Afabicin)
Povidone: 34.65
L-Histidine: 112.65
Sodium Lauryl Sulfate: 30.00
Crospovidone: 15.75
External Phase:
Isomalt: 75.63
Crospovidone: 10.51
Colloidal Silica: 2.40
Magnesium Stearate: 18.00

Another particularly preferred embodiment is characterized by the following composition and amounts (indications in mg/tablet):

Internal Phase:
Afabicin Olamine: 300.41 (corresponding to 240.00 mg of Afabicin)
Povidone: 34.65
L-Histidine: 112.65
Sodium Lauryl Sulfate: 30.00
Crospovidone: 15.75
External Phase:
Mannitol: 75.63
Crospovidone: 10.51
Colloidal Silica: 2.40
Magnesium Stearate: 18.00

The above-mentioned specific preferred embodiments characterize pharmaceutical compositions that are in the form of tablets. These tablets can be used in the uncoated form as described above, or they can be further coated for instance to improve their chemical stability or their aesthetic appearance. For instance, the tablets may be coated with 2-9 parts by weight relative to the uncoated tablet being 100 parts by weight of a coating composition comprising polyvinyl alcohol combined with a second film forming agent, a colorant and/or pigment as well as an anti-taking agent and plasticizing agent.

Of course, such particularly preferred embodiments may additionally fulfil further features described as preferred elsewhere in the present specification or described in the appended claims.

EXAMPLES

Examples 1 to 8 and Comparative Examples 1 to 11

Tablets with an internal phase and an external phase are manufactured by wet granulation using the materials and methods specified in Tables 1, 2, 3 and 4 below.

TABLE 1

| Components | Example 1 (mg/tablet) | Example 2 (mg/tablet) | Example 3 (mg/tablet) | Example 4 (mg/tablet) | Comparative Example 1 (mg/tablet) | Function |
|---|---|---|---|---|---|---|
| Internal Phase | | | | | | |
| Afabicin BES [1] | 40.00 (50.07) [1] | 20.00 (25.03) [1] | 40.00 (50.07) [1] | 40.00 (50.07) [1] | 40.00 (50.07) [1] | Active ingredient |
| Povidone | 5.78 | 2.89 | 5.78 | 5.78 | 5.78 | Binder |
| L-Histidine | 18.78 | 9.39 | 18.78 | 18.78 | / | Histidine compound |
| Sodium lauryl sulfate | 5.00 | / | 5.00 | 5.00 | 5.00 | Surfactant |
| Crospovidone | 2.62 | 1.31 | 2.62 | 2.62 | 2.62 | Disintegrant |
| External Phase | | | | | | |
| Isomalt | 12.60 | 5.82 | / | / | 31.38 | Diluent |
| Mannitol | / | / | / | 12.60 | / | |
| Crospovidone | 1.75 | 0.88 | 1.75 | 1.75 | 1.75 | Disintegrant |
| Colloidal silica | 0.40 | 0.20 | 0.40 | 0.40 | 0.4 | Glidant |
| Magnesium stearate | 3.00 | 1.5 | 3.00 | 3.00 | 3.00 | Lubricant |
| Total weight (mg) | 100.00 | 47.50 | 87.40 | 100.00 | 100.00 | |

[1] Free acid/BES salt ratio = 0.7989; total weight of the free acid/BES salt compound = 50.07 (25.03 in Example 2)

TABLE 2

| Components | Comparative Example 2 (mg/tablet) | Comparative Example 3 (mg/tablet) | Comparative Example 4 (mg/tablet) | Function |
|---|---|---|---|---|
| Internal Phase | | | | |
| Afabicin BES [1] | 40.00 (50.07) [1] | 40.00 (50.07) [1] | 40.00 (50.07) [1] | Active ingredient |
| Povidone | 5.78 | 5.78 | 5.78 | Binder |
| Sodium phosphate monobasic | 0.07 | / | / | Buffer |
| Sodium phosphate dibasic | 0.03 | / | / | Buffer |
| L-Histidine | / | / | / | Histidine compound |
| Calcium phosphate tribasic | / | 18.78 | / | Buffer/Diluent |
| Sodium bicarbonate | / | / | 18.78 | Buffer/Diluent |
| Mannitol | 18.73 | / | / | Diluent |
| Sodium lauryl sulfate | 4.99 | 5.00 | 5.00 | Surfactant |
| Crospovidone | 2.62 | 2.62 | 2.62 | Disintegrant |

TABLE 2-continued

| Components | Comparative Example 2 (mg/tablet) | Comparative Example 3 (mg/tablet) | Comparative Example 4 (mg/tablet) | Function |
|---|---|---|---|---|
| External Phase | | | | |
| Isomalt | 12.58 | 12.60 | 12.60 | Diluent |
| Crospovidone | 1.75 | 1.75 | 1.75 | Disintegrant |
| Colloidal silica | 0.40 | 0.40 | 0.40 | Glidant |
| Magnesium stearate | 2.99 | 3.00 | 3.00 | Lubricant |
| Total weight (mg) | 100.00 | 100.00 | 100.00 | |

[1] Free acid/BES salt ratio = 0.7989; total weight of the free acid/BES salt compound = 50.07

TABLE 3

| Components | Comparative Example 5 (mg/tablet) | Comparative Example 6 (mg/tablet) | Comparative Example 7 (mg/tablet) | Comparative Example 8 (mg/tablet) | Comparative Example 9 (mg/tablet) | Comparative Example 10 (mg/tablet) | Comparative Example 11 (mg/tablet) | Function |
|---|---|---|---|---|---|---|---|---|
| Internal Phase | | | | | | | | |
| Afabicin BES[1] | 40.00 (50.07)[1] | 40.00 (50.07)[1] | 40.00 (50.07)[1] | 40.00 (50.07)[1] | 40.00 (50.07)[1] | 40.00 (50.07)[1] | 40.00 (50.07)[1] | Active ingredient |
| Povidone | 5.78 | 5.78 | 5.78 | 5.78 | 5.78 | 5.78 | 5.78 | |
| L-Histidine | / | / | / | / | / | / | / | Histidine compound |
| Glycine | 18.78 | / | / | / | / | / | / | Histidine alternative |
| L-arginine | / | 18.78 | / | / | / | / | / | Histidine compound alternative |
| Imidazole | / | / | 18.78 | / | / | / | / | Histidine compound alternative |
| L-alanine | / | / | / | 8.13 | / | / | / | Histidine compound alternative |
| L-tryptophan | / | / | / | 10.65 | / | / | / | Histidine compound alternative |
| L-tyrosine | / | / | / | / | 18.78 | / | / | Histidine compound alternative |
| L-proline | / | / | / | / | / | 18.78 | / | Histidine compound alternative |
| Benzoic acid | / | / | / | / | / | / | 18.78 | Histidine compound alternative |
| Sodium lauryl sulfate | 5.00 | 5.00 | 5.00 | 5.00 | 5.00 | 5.00 | 5.00 | Surfactant |
| Crospovidone | 2.62 | 2.62 | 2.62 | 2.62 | 2.62 | 2.62 | 2.62 | Disintegrant |
| External Phase | | | | | | | | |
| Isomalt | 12.60 | 12.60 | 12.60 | 12.60 | 12.60 | 12.60 | 12.60 | Diluent |
| Crospovidone | 1.75 | 1.75 | 1.75 | 1.75 | 1.75 | 1.75 | 1.75 | Disintegrant |
| Colloidal silica | 0.40 | 0.40 | 0.40 | 0.40 | 0.40 | 0.40 | 0.40 | Glidant |
| Magnesium stearate | 3.00 | 3.00 | 3.00 | 3.00 | 3.00 | 3.00 | 3.00 | Lubricant |
| Total Weight | 100.00 | 100.00 | 100.00 | 100.00 | 100.00 | 100.00 | 100.00 | |

[1] Free acid/BES salt ratio = 0.7989; total weight of the free acid/BES salt compound = 50.07

TABLE 4

| Components | Example 5 (mg/tablet) | Example 6 (mg/tablet) | Example 7 (mg/tablet) | Example 8 (mg/tablet) | Function |
|---|---|---|---|---|---|
| Internal Phase | | | | | |
| Afabicin BES [1] | 40.00 (50.07)[1] | 40.00 (50.07)[1] | 40.00 (50.07)[1] | 40.00 (50.07)[1] | Active ingredient |
| Povidone | 5.78 | 5.78 | 5.78 | 5.78 | Binder |
| L-Histidine | 9.59 | 12.78 | 15.98 | 63.93 | Histidine compound |
| Sodium lauryl sulfate | 5.00 | 5.00 | 5.00 | 5.00 | Surfactant |
| Crospovidone | 2.62 | 2.62 | 2.62 | 2.62 | Disintegrant |
| External Phase | | | | | |
| Isomalt | 12.60 | 12.60 | 12.60 | 12.60 | Diluent |
| Crospovidone | 1.75 | 1.75 | 1.75 | 1.75 | Disintegrant |
| Colloidal silica | 0.40 | 0.40 | 0.40 | 0.40 | Glidant |
| Magnesium stearate | 3.00 | 3.00 | 3.00 | 3.00 | Lubricant |
| Total weight (mg) | 90.81 | 94.00 | 97.20 | 145.15 | |

[1] Free acid/BES salt ratio = 0.7989; total weight of the free acid/BES salt compound = 50.07 (25.03 in Example 2)

The dissolution characteristics of the above pharmaceutical compositions are determined by an in vitro experiment using a Fasted-State Simulated Gastric Fluid (FaSSGF) with 60 min. This discriminatory method is best suited for testing compositions containing up to 40 mg of Afabicin, due to limited solubility of the active pharmaceutical ingredient. Hence, even if there is an intention to develop a pharmaceutical composition containing a greater amount of Afabicin, it is recommended to proportionally scale the amounts of all components down (such that relative amounts remain unchanged and such that the Afabicin content is not higher than 40 mg), test this pharmaceutical composition and then extrapolate from the obtained test results to the pharmaceutical composition of interest.

The dissolution test was performed in a basket Apparatus 1 at the following conditions:
Temperature: 37.0° C.±0.5° C.
Rotation speed: 100 rpm during 45 min, then 15 min at 250 rpm
Dissolution medium and volume: 1000 mL FaSSGF
Number of units tested: 3 or 6

Figure 2:
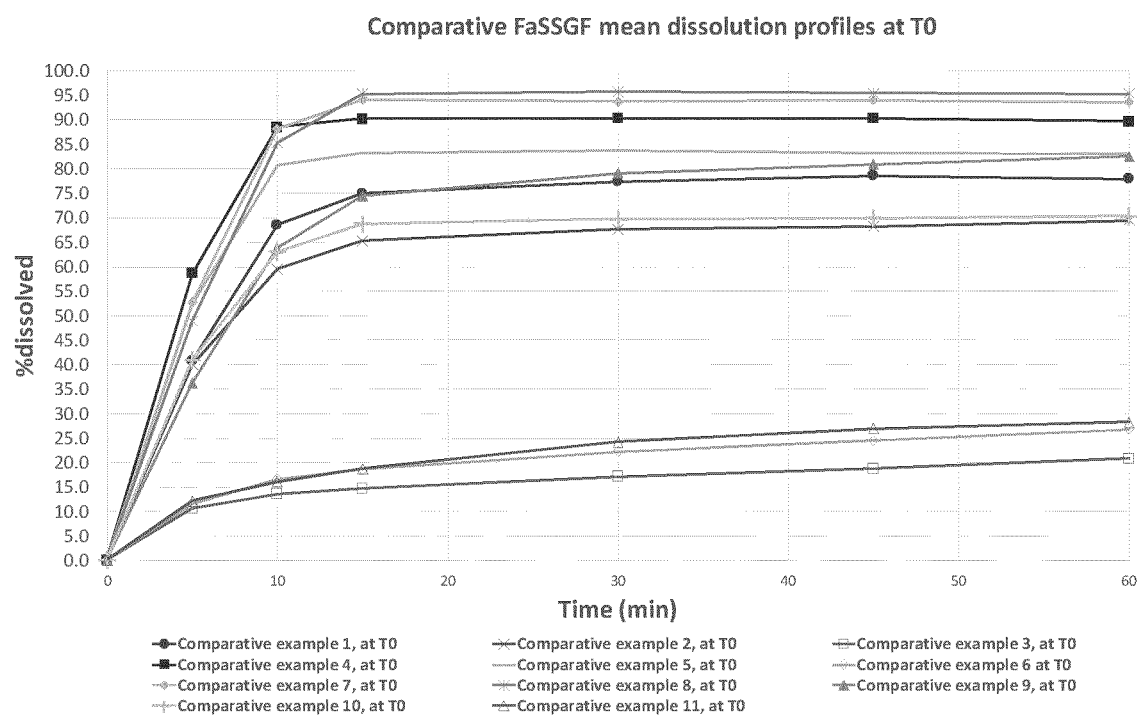
FIG. 2: In vitro dissolution profile of Comparative Examples 1 to 11 after manufacturing (T0)
Figure 3:
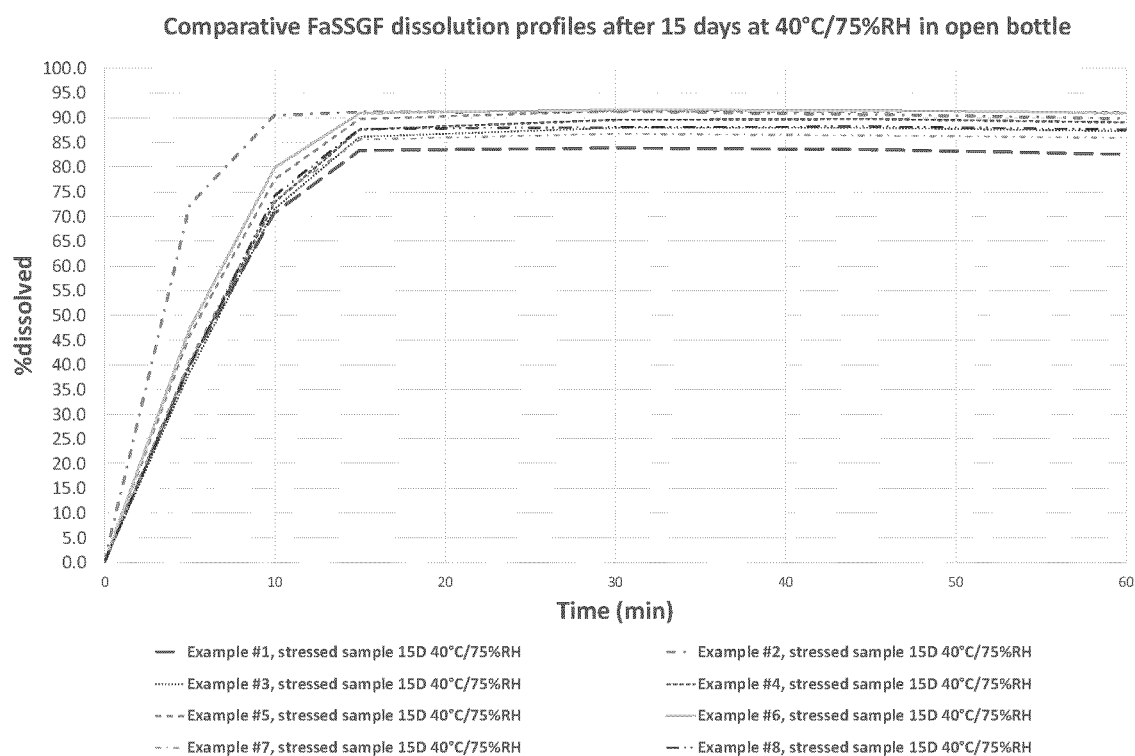
FIG. 3: In vitro dissolution profile of Examples 1 to 8 after accelerated storage conditions (15 days at 40° C./75% RH in open bottle)
Figure 4:
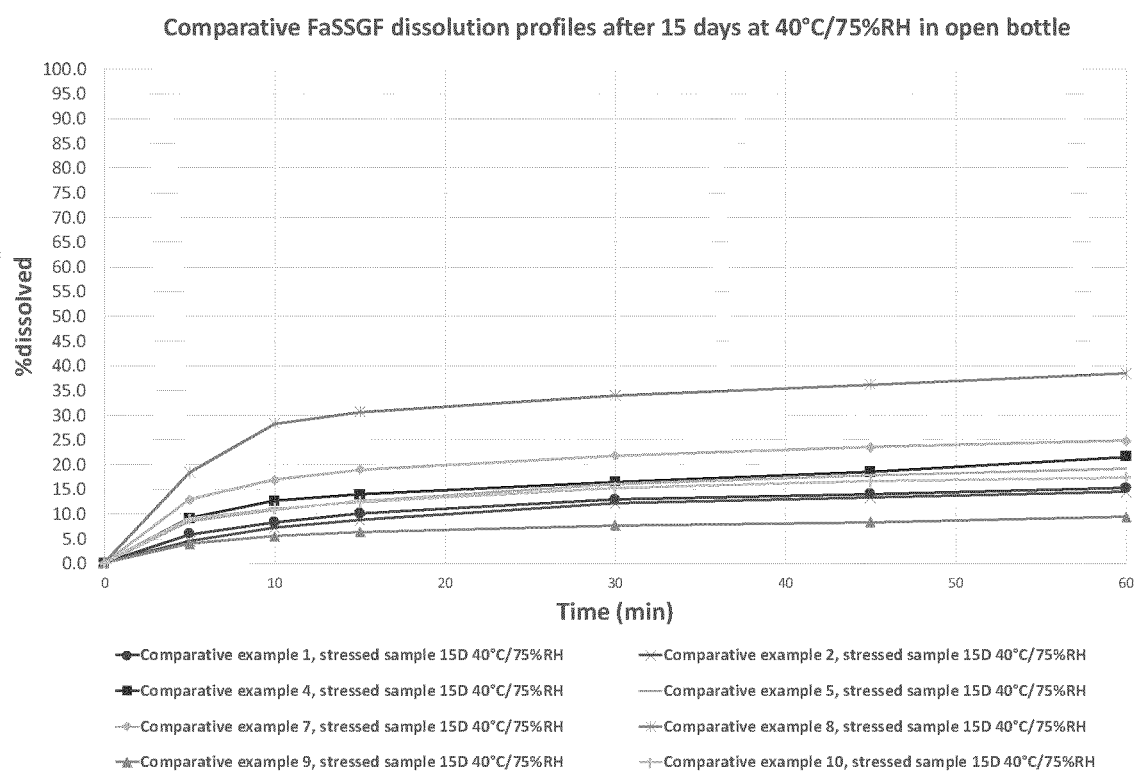
FIG. 4: In vitro dissolution profile of Comparative Examples 1, 2, 4, 5, 7, 8, 9, and 10 after accelerated storage conditions (15 days at 40° C./75% RH in open bottle)

The results of this experiment are shown in FIGS. 1, 2, 3 and 4. FIGS. 1 and 2 show the dissolution characteristics before storing the samples under stress conditions. FIGS. 2 and 3 show the dissolution characteristics after storage under stress conditions for those samples that exhibited satisfactory dissolution before storage. These results confirm the small difference of in vitro dissolution profile between the eight inventive compositions: Examples 1 to 8 exhibited quick dissolution over time (initially and after stress conditions of 15 days at 40° C./75% RH). These results are assessed to be satisfactory. By contrast, FIG. 2 shows slow initial dissolution for Comparative Examples 3, 6 and 11 but relatively fast initial dissolution for the remaining Comparative Examples 1, 2, 4, 5, 7, 8, 9, and 10. However, all Comparative Examples 1, 2, 4, 5, 7, 8, 9, and 10 exhibited slow dissolution after storage under stress conditions, as shown in FIG. 4. These slow dissolution characteristics are assessed to be non-satisfactory.

The invention claimed is:

1. A solid pharmaceutical composition in the form of a unit dose comprising Afabicin or a pharmaceutically acceptable salt thereof and one or more pharmaceutically acceptable excipients, characterized in that the composition contains a histidine compound,
wherein the composition shows more rapid dissolution compared with a composition lacking histidine comprising the same components.

2. The solid pharmaceutical composition according to claim 1, which comprises Afabicin or a pharmaceutically acceptable salt thereof in an amount from 20 mg to 480 mg.

3. The solid pharmaceutical composition according to claim 1, which contains histidine.

4. The solid pharmaceutical composition according claim 1, which is in the form of a tablet, the tablet comprising an internal phase and an external phase, wherein Afabicin or a pharmaceutically acceptable salt thereof is contained only in the internal phase.

5. The solid pharmaceutical composition according to claim 4, which contains the histidine compound only in the internal phase.

6. The solid pharmaceutical composition according to claim 1, which contains a binder selected from the group consisting of povidone, copovidone, poloxamer, polyethylene glycol, magnesium aluminosilicate, gelatin, acacia, dextrin, dextrates, dextrose, polydextrose, guar gum, hydrogenated vegetable oil, liquid glucose, wax, maltose, sucrose, lactose, wax, and mixtures thereof.

7. The solid pharmaceutical composition according to claim 1, which contains a diluent selected from the group consisting of mannitol, isomalt, lactose, calcium phosphate, calcium carbonate, calcium sulfate, sucrose, fructose, maltose, xylitol, maltitol, lactitol, trehalose, aluminum silicate, cyclodextrin, dextrose, polydextrose, glucose, dextrin, dextrates, magnesium carbonate and mixtures thereof.

8. The solid pharmaceutical composition according to claim 1, which contains a surfactant selected from the group consisting of sodium lauryl sulfate, poloxamers, sodium docusate, sodium deoxycholate, sorbitan esters, sucrose esters of fatty acid, tyloxapol, lecithin, polysorbate, and mixtures thereof.

9. The solid pharmaceutical composition according to claim 1, which contains a disintegrant selected from the group consisting of crospovidone, magnesium aluminosilicate, colloidal silicon dioxide, guar gum and mixtures thereof.

10. The solid pharmaceutical composition according to claim 1, which is in the form of a capsule containing Afabicin or a pharmaceutically acceptable salt thereof and one or more pharmaceutically acceptable excipients in the form of a powder or granulate.

11. The solid pharmaceutical composition according to claim 1, which is adapted for oral administration.

12. The solid pharmaceutical composition according to claim 1, which is in the form of a tablet or capsule.

13. A method of manufacturing the solid composition according to claim 1, which comprises the following steps in the specified order:
(i) dry mixing some or all of the components of the composition;
(ii) granulating the resulting mixture to obtain a granulate;
(iii) admixing any remaining components of the composition to the granulate;
(iv) compression of the resulting mixture to obtain a compressed tablet; and
(v) optionally coating the resulting compressed tablet.

14. The method according to claim 13, wherein the granulation step is performed by wet granulation or dry granulation.

15. The method according to claim 13, wherein at least one of the following conditions is fulfilled:
(a) diluent is present and a part of the diluent is admixed to the granulate of step (ii);
(b) disintegrant is present and a part of the disintegrant is admixed to the granulate of step (ii);
(c) glidant is present and a part of or all of the glidant is admixed to the granulate of step (ii); and/or
(d) lubricant is present and a part of or all of the lubricant is admixed to the granulate of step (ii).

16. A method of treating bacterial infection in a mammal, comprising administering to the mammal a solid pharmaceutical composition according to claim 1, wherein the bacterial infection is caused by the bacterial species *S. aureus*.

17. The method according to claim 16, wherein the mammal is a human.

18. The method according to claim 16, wherein the bacterial infection is acute bacterial skin and skin-structure infection (ABSSI) or bacterial infection associated with diabetic foot syndrome.

* * * * *